US011739452B2

(12) United States Patent
Taylor et al.

(10) Patent No.: US 11,739,452 B2
(45) Date of Patent: *Aug. 29, 2023

(54) TIME-DEPENDENT SYNTHETIC BIOLOGICAL BARRIER MATERIAL

(71) Applicant: POLY-MED, INC., Anderson, SC (US)

(72) Inventors: Michael Scott Taylor, Anderson, SC (US); Seth Dylan McCullen, Greenville, SC (US); David Shalaby, Southfield, MA (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/115,650

(22) PCT Filed: Jan. 30, 2015

(86) PCT No.: PCT/US2015/013732
§ 371 (c)(1),
(2) Date: Jul. 29, 2016

(87) PCT Pub. No.: WO2015/116917
PCT Pub. Date: Aug. 6, 2015

(65) Prior Publication Data
US 2017/0167064 A1 Jun. 15, 2017

Related U.S. Application Data

(60) Provisional application No. 61/933,578, filed on Jan. 30, 2014.

(51) Int. Cl.
| | |
|---|---|
| *A61F 2/00* | (2006.01) |
| *A61L 31/06* | (2006.01) |
| *A61L 31/12* | (2006.01) |
| *A61L 31/14* | (2006.01) |
| *D04H 1/4382* | (2012.01) |
| *D04H 1/728* | (2012.01) |

(52) U.S. Cl.
CPC .......... *D04H 1/728* (2013.01); *A61F 2/0063* (2013.01); *A61L 31/06* (2013.01); *A61L 31/129* (2013.01); *A61L 31/14* (2013.01); *A61L 31/148* (2013.01); *D04H 1/43835* (2020.05); *A61F 2210/0004* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 4,646,741 A | 3/1987 | Smith | |
| 7,172,765 B2* | 2/2007 | Chu | A61K 9/0024 424/423 |
| 8,048,446 B2* | 11/2011 | Lelkes | A61L 27/26 424/422 |
| 8,128,954 B2 | 3/2012 | Davis et al. | |
| 9,011,439 B2 | 4/2015 | Shalaby et al. | |
| 9,492,593 B2 | 11/2016 | Shalaby | |
| 10,004,833 B2 | 6/2018 | Shalaby | |
| 10,751,449 B2 | 8/2020 | Shalaby | |
| 11,197,950 B2 | 12/2021 | Shalaby | |
| 11,486,058 B2 | 11/2022 | Taylor et al. | |
| 2002/0173213 A1 | 11/2002 | Chu et al. | |
| 2003/0168756 A1 | 9/2003 | Balkus et al. | |
| 2003/0228350 A1 | 12/2003 | Chu et al. | |
| 2005/0070930 A1* | 3/2005 | Kammerer | A61F 2/0063 606/151 |
| 2005/0149158 A1 | 7/2005 | Hunter et al. | |
| 2006/0085063 A1 | 4/2006 | Shastri et al. | |
| 2006/0240063 A9 | 10/2006 | Hunter et al. | |
| 2006/0263417 A1 | 11/2006 | Lelkes | |
| 2006/0264140 A1 | 11/2006 | Andrady et al. | |
| 2008/0095748 A1 | 4/2008 | Kharazi et al. | |
| 2008/0220054 A1* | 9/2008 | Shastri | A61K 9/0092 424/443 |
| 2010/0143652 A1 | 6/2010 | Stockton et al. | |
| 2010/0166854 A1 | 7/2010 | Michnial-Kohn et al. | |
| 2010/0261799 A1 | 10/2010 | Vachon et al. | |

(Continued)

FOREIGN PATENT DOCUMENTS

| | | |
|---|---|---|
| EP | 0707044 | 4/1996 |
| JP | 2004321484 | 4/2003 |

(Continued)

OTHER PUBLICATIONS

Thompson, Transactions of the Faraday Society, RSC, 52, 1956 (Year: 1956).*
International Search Report and Written Opinion for PCT/US2015/013732 dated Apr. 22, 2015.
Extended European Search Report for Application No. 15743098.4 dated Jul. 21, 2017.
Notice of Allowance, dated Jun. 5, 2019, for EP 15743098.4, inventor, Penniston, et al., (7 pgs).
Office Action, dated Nov. 20, 2018, for EP 15743098.4, inventor, Penniston, et al., (4 pgs).
Notice of Loss of Rights, dated Mar. 28, 2018, for EP 15743098.4, inventor, Penniston, et al., (1 pg).
Office Action, dated Dec. 6, 2018, for JP 2016-567459, inventor, Penniston, et al., (4 pgs).

(Continued)

*Primary Examiner* — Robert A Wax
*Assistant Examiner* — William Craigo
(74) *Attorney, Agent, or Firm* — Mary Anthony Merchant; Meunier Carlin & Curfman LLC

(57) ABSTRACT

Thermally stable absorbable fiber populations, i.e. fiber populations that do not undergo thermally induced crystallization, can be intermixed to yield a stabilizing effect without altering morphological properties of a first fiber system. By addition of a stabilizing fiber population one may minimize thermally induced shrinkage and maintain physical properties of electrospun materials in the as-formed state. In one particular abstract, medical barrier materials may be formed from the electrospun materials to provide improved medical barriers for treatments.

10 Claims, 21 Drawing Sheets

(56) References Cited

U.S. PATENT DOCUMENTS

| | | | | |
|---|---|---|---|---|
| 2011/0143429 | A1* | 6/2011 | Chun | A61L 27/18 |
| | | | | 435/325 |
| 2012/0068384 | A1* | 3/2012 | Phaneuf | A61K 9/0092 |
| | | | | 264/466 |
| 2012/0088424 | A1 | 4/2012 | Moore et al. | |
| 2012/0315225 | A1* | 12/2012 | Porbeni | A61L 15/26 |
| | | | | 424/49 |
| 2013/0253663 | A1* | 9/2013 | Amoroso | C08L 75/00 |
| | | | | 623/23.75 |
| 2013/0267137 | A1 | 10/2013 | Peniston et al. | |
| 2013/0267972 | A1 | 10/2013 | Peniston et al. | |
| 2014/0141152 | A1 | 5/2014 | Sostek et al. | |
| 2014/0271795 | A1* | 9/2014 | Phaneuf | A61K 31/496 |
| | | | | 424/443 |
| 2015/0211151 | A1 | 7/2015 | Taylor | |
| 2017/0167054 | A1 | 6/2017 | Taylor et al. | |
| 2019/0330768 | A1 | 10/2019 | Taylor et al. | |

FOREIGN PATENT DOCUMENTS

| | | |
|---|---|---|
| JP | 2004-321484 | 11/2004 |
| WO | 2006116000 | 11/2006 |
| WO | WO2006/116000 | 11/2006 |
| WO | 2010143646 | 12/2010 |
| WO | WO2015/116912 | 8/2015 |

OTHER PUBLICATIONS

Office Action, dated Jun. 20, 2019, for JP 2016-567459, inventor, Penniston, et al., (4 pgs).
PCT/US2015/013732, PCT, Jan. 30, 2015, Taylor.
2937954, Canada, Jan. 30, 2015, Taylor.
15743098.4, EPO, Jan. 30, 2015, Taylor.
2016-567459, Japan, Jan. 30, 2015, Taylor.
Extended European Search Report, dated Mar. 12, 2020, in European Patent Application 19205535.8-1102, 5 Pages.
Sigma-Aldrich, Chemical Structures, provided Jul. 18, 2017, (2 p.).
Patent Certificate, issued May 3, 2022, in CA Patent 2937954, filed Jan. 30, 2015, (2 p.).
Notice of Allowance, dated Dec. 20, 2021, in CA Patent 2937954, filed Jan. 30, 2015, (2 p.).
Office Action, dated Feb. 22, 2014, in CA Patent 2937954, filed Jan. 30, 2015, (4 p.).
Decision to Grant, dated Oct. 4, 2019, in EPO Patent Application No. 15743098.4, filed Jan. 30, 2015, (2 p.).
Office Action, dated Nov. 19, 2018, in EPO Patent Application No. 15743098.4, filed Jan. 30, 2015, (4 p.).
Office Action, dated Apr. 9, 2021, in EPO Application 19205535.8, filed Oct. 28, 2019, (5 p.).
Certificate of Patent, issued Feb. 19, 2020, in JP Patent 6663858, issued Feb. 19, 2020, (2 p.).
English Translation of Office Action, dated Jul. 16, 2019, in JP Patent 6663858, dated Feb. 19, 2020, (4 p.).
English Translation of Office Action, dated Dec. 19, 2018, in JP Patent 6663858, dated Feb. 19, 2020, (7 p.).
Letter re Patent Grant, dated Mar. 13, 2020, in JP Application No. 2020-023988, filed Feb. 17, 2020, (1 p.).
Office Action, dated May 27, 2021, in JP Application No. 2020-023988, filed Feb. 17, 2020, (5 p.).
Response to NonFinal Office Action, dated May 5, 2022, in U.S. Appl. No. 14/610,130, filed Jan. 30, 2015, (6 p.).
NonFinal Office Action, dated Dec. 7, 2021, in U.S. Appl. No. 14/610,130, filed Jan. 30, 2015, (9 p.).
Response to Final Office Action—RCE, dated Oct. 25, 2021, in U.S. Appl. No. 14/610,130, filed Jan. 30, 2015, (13 p.).
Final Office Action, dated Jun. 25, 2021, in U.S. Appl. No. 14/610,130, filed Jan. 30, 2015, (9 p.).
Response to NonFinal Office Action, dated Apr. 23, 2021, in U.S. Appl. No. 14/610,130, filed Jan. 30, 2015, (10 p.).
NonFinal Office Action, dated Dec. 23, 2020, in U.S. Appl. No. 14/610,130, filed Jan. 30, 2015, (10 p.).
Response to Final Office Action—RCE, issued Jul. 16, 2020, in U.S. Appl. No. 14/610,130, filed Jan. 30, 2015, (14 p.).
Final Office Action, dated Apr. 16, 2020, in U.S. Appl. No. 14/610,130, filed Jan. 30, 2015, (11 p.).
Response to NonFinal Office Action, dated Dec. 27, 2019, in U.S. Appl. No. 14/610,130, filed Jan. 30, 2015, (12 p.).
Notice of NonCompliant Response, dated Dec. 23, 2019, in U.S. Appl. No. 14/610,130, filed Jan. 30, 2015, (3 p.).
Response to Nonfinal Office Action, dated Dec. 16, 2019, in U.S. Appl. No. 14/610,130, filed Jan. 30, 2015, (14 p.).
NonFinal Office Action, dated Sep. 19, 2019, in U.S. Appl. No. 14/610,130, filed Jan. 30, 2015, (6 p.).
Response to Final Office Action—RCE, dated Jul. 3, 2019, in U.S. Appl. No. 14/610,130, filed Jan. 30, 2015, (19 p.).
Applicant Interview Summary, dated Apr. 18, 2019, in U.S. Appl. No. 14/610,130, filed Jan. 30, 2015, (7 p.).
Final Office Action, dated Jan. 24, 2019, in U.S. Appl. No. 14/610,130, filed Jan. 30, 2015, (19 p.).
Response to NonFinal Office Action, dated Sep. 27, 2018, in U.S. Appl. No. 14/610,130, filed Jan. 30, 2015, (6 p.).
NonFinal Office Action, dated Jun. 27, 2018, in U.S. Appl. No. 14/610,130, filed Jan. 30, 2015, (18 p.).
Response to Final Office Action—RCE, dated May 10, 2018, in U.S. Appl. No. 14/610,130, filed Jan. 30, 2015, (17 p.).
Final Office Action, dated Feb. 22, 2018, in U.S. Appl. No. 14/610,130, filed Jan. 30, 2015, (18 p.).
Response to NonFinal Office Action, dated Nov. 20, 2017, in U.S. Appl. No. 14/610,130, filed Jan. 30, 2015, (13 p.).
NonFinal Office Action, dated Jul. 18, 2017, in U.S. Appl. No. 14/610,130, filed Jan. 30, 2015, (17 p.).
Response to Final Office Action—RCE, dated Jun. 6, 2022, in U.S. Appl. No. 16/823,674, filed Mar. 19, 2020, (13 p.).
Final Office Action, dated Apr. 28, 2022, in U.S. Appl. No. 16/823,674, filed Mar. 19, 2020, (6 p.).
Response to NonFinal Office Action, dated Dec. 23, 2021, in U.S. Appl. No. 16/823,674, filed Mar. 19, 2020, (11 p.).
NonFinal Office Action, dated Sep. 16, 2021, in U.S. Appl. No. 16/823,674, filed Mar. 19, 2020, (8 p.).
Preliminary Amendment, dated Mar. 19, 2020, in U.S. Appl. No. 16/823,674, filed Mar. 19, 2020, (7 p.).
Notice of Abandonment, dated Aug. 20, 2019, in U.S. Appl. No. 15/115,645, filed Jul. 29, 2016, (2 p.).
Applicant Interview, dated Apr. 15, 2019, in U.S. Appl. No. 15/115,645, filed Jul. 29, 2016, (3 p.).
Final Office Action, dated Feb. 14, 2019, in U.S. Appl. No. 15/115,645, filed Jul. 29, 2016, (6 p.).
Response to NonFinal Office Action, dated Nov. 26, 2018, in U.S. Appl. No. 15/115,645, filed Jul. 29, 2016, (9 p.).
NonFinal Office Action, dated Jul. 25, 2018, in U.S. Appl. No. 15/115,645, filed Jul. 29, 2016, (7 p.).
RCE, dated Jun. 7, 2018, in U.S. Appl. No. 15/115,645, filed Jul. 29, 2016, (3 p.).
Advisory Action, dated May 22, 2018, in U.S. Appl. No. 15/115,645, filed Jul. 29, 2016, (4 p.).
Response to Final Office Action, dated Apr. 9, 2018, in U.S. Appl. No. 15/115,645, filed Jul. 29, 2016, (7 p.).
Final Office Action, dated Feb. 7, 2018, in U.S. Appl. No. 15/115,645, filed Jul. 29, 2016, (7 p.).
Response to NonFinal Office Action, dated Dec. 27, 2017, in U.S. Appl. No. 15/115,645, filed Jul. 29, 2016, (7 p.).
NonFinal Office Action, dated Sep. 27, 2017, in U.S. Appl. No. 15/115,645, filed Jul. 29, 2016, (9 p.).
NonFinal Office Action, dated Mar. 28, 2022, in U.S. Appl. No. 16/411,279, filed May 14, 2019, (8 p.).
Response to Final Office Action—RCE, dated Dec. 20, 2021, in U.S. Appl. No. 16/411,279, filed May 14, 2019, (13 p.).
Advisory Action, dated Dec. 17, 2021, in U.S. Appl. No. 16/411,279, filed May 14, 2019, (4 p.).
Response to Final Office Action, dated Nov. 22, 2021, in U.S. Appl. No. 16/411,279, filed May 14, 2019, (12 p.).

(56) References Cited

OTHER PUBLICATIONS

Final Office Action, dated Sep. 21, 2021, in U.S. Appl. No. 16/411,279, filed May 14, 2019, (8 p.).
Response to NonFinal Office Action, dated Jul. 26, 2021, in U.S. Appl. No. 16/411,279, filed May 14, 2019, (14 p.).
NonFinal Office Action, dated Apr. 26, 2021, in U.S. Appl. No. 16/411,279, filed May 14, 2019, (7 p.).
Response to Restriction Requirement, dated Apr. 6, 2021, in U.S. Appl. No. 16/411,279, filed May 14, 2019, (7 p.).
Restriction Requirement, dated Feb. 10, 2021, in U.S. Appl. No. 16/411,279, filed May 14, 2019, (6 p.).
Preliminary Amendment, dated Jul. 22, 2019, in U.S. Appl. No. 16/411,279, filed May 14, 2019, (7 p.).
International Preliminary Report on Patentability, dated Aug. 11, 2016, in PCT Application No. PCT/US2015/013723, filed Jan. 30, 2015, (6 p.).
International Search Report, dated Jun. 16, 2015, in PCT Application No. PCT/US2015/013723, filed Jan. 30, 2015, (4 p.).
Sell et al., Extracellular matrix regenerated: Tissue engineering via electrospun biomimetic nanofibers, Polym. Int., vol. 56, 1349-1360, 2007.
PCT/US2015/013723, PCT, Jan. 30, 2015, Taylor.
U.S. Appl. No. 15/115,645, filed Jul. 29, 2016, Taylor.
U.S. Appl. No. 16/411,279, filed May 4, 2019, Taylor.
U.S. Appl. No. 61/933,596, filed Jan. 30, 2014, Taylor.
U.S. Appl. No. 14/610,130, filed Jan. 30, 2015, Taylor.
U.S. Appl. No. 16/823,674, filed Jan. 30, 2015, Taylor.

* cited by examiner

FIGURE 12

| Elongation at Break (N) | Day 0 | Day 3 | Day 5 | Day 7 |
|---|---|---|---|---|
| PGLA | | | | |
| Sample 1 | 307 | 48.7 | 28.3 | 12.3 |
| Sample 2 | 334 | 42.7 | 42.8 | 15.9 |
| Sample 3 | 294 | 38.6 | 13.3 | 13.1 |
| Average | 311.6667 | 43.3333 | 14.8667 | 13.7667 |
| Standard Deviation | 20.4625 | 5.07888 | 7.27759 | 3.42136 |
| Percent | 100% | 14% | 12% | 5% |
| Standard Deviation | 7% | 2% | 2% | 1% |

| Elongation at Break (N) | Day 0 | Day 3 | Day 5 | Day 7 |
|---|---|---|---|---|
| PDO | | | | |
| Sample 1 | 289 | 286 | 204 | 182.3 |
| Sample 2 | 319 | 306 | 148 | 159.4 |
| Sample 3 | 311 | 250 | 151 | 184.7 |
| Average | 306.3333 | 280.6667 | 167.6667 | 174.9667 |
| Standard Deviation | 20.0821 | 28.3784 | 31.5074 | 15.6214 |
| Percent | 100% | 86% | 52% | 56% |
| Standard Deviation | 6% | 9% | 10% | 4% |

| Elongation at Break (N) | Day 0 | Day 3 | Day 5 | Day 7 |
|---|---|---|---|---|
| PGLA/PDO | | | | |
| Sample 1 | 303 | 129 | 66.4 | 43.1 |
| Sample 2 | 289 | 111 | 85 | 73.7 |
| Sample 3 | 293 | 108.4 | 48.4 | 30.8 |
| Average | 287.3333 | 116.1333 | 66.6 | 49.2 |
| Standard Deviation | 18.2893 | 11.2184 | 18.8060 | 22.0099 |
| Percent | 100% | 40% | 23% | 17% |
| Standard Deviation | 6% | 4% | 6% | 8% |

FIGURE 14

| Suture Pull-Out Strength vs Time PGLA | Day 0 | Day 3 | Day 5 | Day 7 |
|---|---|---|---|---|
| Sample 1 | 3.9 | 3.23 | 1.07 | 0.47 |
| Sample 2 | 3.73 | 1.36 | 1.47 | 0.5 |
| Sample 3 | 3.8 | 1.98 | 1.76 | 1 |
| Average | 3.81000 | 2.19 | 1.43333 | 0.65667 |
| Standard Deviation | 0.08327 | 0.95093 | 0.34645 | 0.29714 |
| Percent | 100% | 58% | 38% | 18% |
| Standard Deviation | 16% | 23% | 8% | 7% |

| Suture Pull-Out Strength vs Time PDO | Day 0 | Day 3 | Day 5 | Day 7 |
|---|---|---|---|---|
| Sample 1 | 2.99 | 3.03 | 3.1 | 3.39 |
| Sample 2 | 2.79 | 2.9 | 2.84 | 2.40 |
| Sample 3 | 2.99 | 2.98 | 2.80 | 2.86 |
| Average | 2.89 | 2.97333 | 2.91333 | 2.87333 |
| Standard Deviation | 0.14142 | 0.06658 | 0.13628 | 0.44816 |
| Percent | 100% | 100% | 98% | 99% |
| Standard Deviation | 5% | 2% | 5% | 16% |

| Suture Pull-Out Strength vs Time PGLA/PDO | Day 0 | Day 3 | Day 5 | Day 7 |
|---|---|---|---|---|
| Sample 1 | 3.03 | 1.98 | 1.31 | 1.5 |
| Sample 2 | 2.77 | 1.86 | 1.2 | 1 |
| Sample 3 | 2.73 | 2.01 | 0.9 | 0.77 |
| Average | 2.84333 | 1.95 | 1.13333 | 1.09 |
| Standard Deviation | 0.47087 | 0.07937 | 0.17363 | 0.37339 |
| Percent | 100% | 69% | 40% | 44% |
| Standard Deviation | 16% | 3% | 7% | 13% |

FIGURE 17

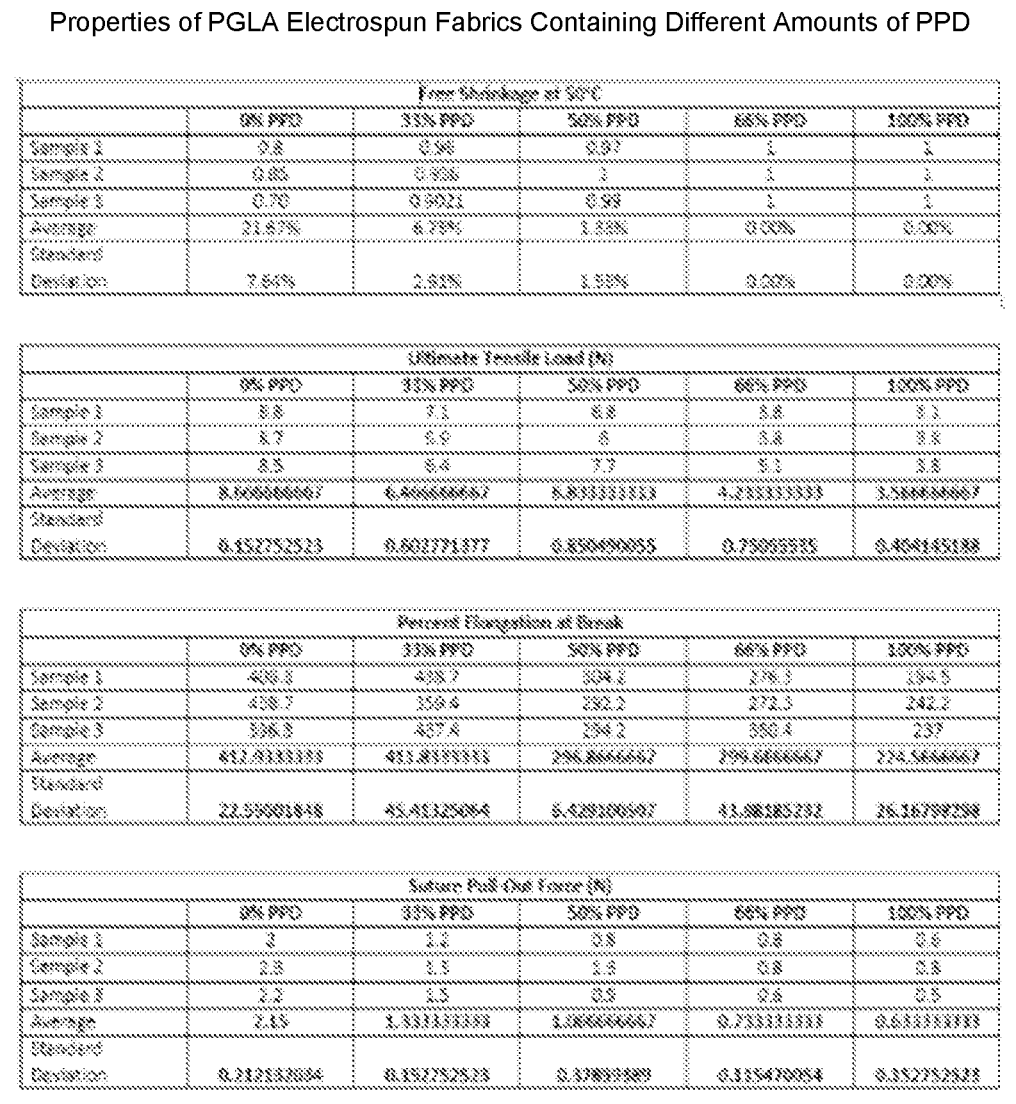

Properties of PGLA Electrospun Fabrics Containing Different Amounts of PPD

FIGURE 18

TIME-DEPENDENT SYNTHETIC BIOLOGICAL BARRIER MATERIAL

CROSS-REFERENCE TO RELATED APPLICATION

This application is a national phase application under 35 U.S.C. § of International Application No. PCT/US2015/013732, filed Jan. 30, 2015, which claims the benefit under 35 U.S.C. § 119(e) of U.S. Provisional Patent Application No. 61/933,578 filed Jan. 30, 2014, the entire content of each of which is incorporated herein by reference.

BACKGROUND OF THE INVENTION

Fibrous materials are capable of providing a barrier for a range of membrane applications including: tissue separation, hernia repair, peritoneum replacement, dura mater replacement, and pelvic floor reconstruction, amongst others. Of these types of tissue replacement, hernia repair is one of the most frequently performed surgical operations in the United States with approximately one million procedures conducted annually.

The vast majority of these membrane applications, including hernia repairs, employ synthetic surgical meshes that are comprised of various arrangements of absorbable and nonabsorbable films, fibers, and yarns, and are primarily based on traditional knit and woven structures. These materials have reduced the frequency of hernia recurrence. Unfortunately, recurrence rates remain high, with up to 15% recurrence reported for inguinal and incisional hernia repair.

In addition, long-term complications such as chronic pain, increased abdominal wall stiffness, fibrosis, and mesh contraction persist following the use of current surgical meshes. These complications dramatically affect patient quality of life. To counteract these complications, medical device technology has moved toward development of synthetic repair meshes consisting of 100% absorbable materials. To date, no significant clinical data is available to determine the viability of such absorbable meshes.

A benefit of absorbable meshes is that they would not need to be removed following surgery and do not disrupt new tissue formation of collagen upon healing. However, preliminary studies with completely absorbable hernia meshes indicate that the replacement collagen layer is not strong enough to prevent hernia recurrence and often results in catastrophic failure. This is most likely due to the relatively fast degradation profile of meshes such as VICRYL knitted mesh, available from Ethicon Inc., a subsidiary of Johnson and Johnson. These meshes degrade in approximately three to four weeks. However, the collagen remodeling process may take several months for it to mature and gain normal or pre-injury strength.

Synthetic barrier materials such as hernia meshes are largely comprised of nondegradable fibrous arrays constructed from either knitted, woven, or nonwoven methodologies. Recently, the electrospinning method has generated significant interest in medical device applications. The process can produce micro-fibrous materials with a topography and size-scale similar to the native extracellular matrix. Electrospun materials are advantageous for a range of applications in the medical device field for tissue replacement, augmentation, drug delivery, among other applications.

During the electrospinning process, a polymer is dissolved in solution and is metered at a controlled flow rate through a capillary or orifice. By applying a critical voltage to overcome the surface tension of the polymer solution, along with sufficient molecular chain entanglement in solution, fiber formation can occur. Application of a critical voltage induces a high charge density forming a Taylor cone, the cone observed in electrospinning, electrospraying and hydrodynamic spray processes, from which a jet of charged particles emanates above a threshold voltage, at the tip of the orifice.

Emerging from the Taylor cone, a rapid whipping instability, or fiber jet, is formed moving at approximately 10 m/s from the orifice to a distanced collector. Due to the high velocity of the fiber jet, fiber formation occurs on the order of milliseconds due to the rapid evaporation of the solvent (i.e., solution electrospinning), inhibiting polymer crystallization. Typically, the ejected jets from the polymer solution is elongated more than 10,000 draw ratio in a time period of 0.05 s. This high elongation ratio is driven by the electric force induced whipping instability, and the polymer chains remain in an elongated state after fiber solidification due to this high elongation and chain confinement within micron-sized fibers.

For semi-crystalline polymers, retarded crystallization may be observed as fast solidification of the stretched polymer chains do not allow time to organize into suitable crystal registration, and is also inhibited by the small fiber diameters. The formation process may impart a significant amount of internal stresses into the resulting fibers. As a result, these materials can undergo both morphological and mechanical property changes when exposed to heat due to cold crystallization as well as stress relief via application of heat. Polymers that display a glass transition temperature (Tg) near or at body temperature (37° C.) are unstable for biological applications due to the uncontrolled transition between a glassy and amorphous state. Exposing temperature sensitive materials to temperatures near or at their Tg ultimately yields crystallization events which have both micro and macroscopic effects on electrospun fabrics.

Electrospun materials may be relatively unstable and may undergo crystallization due to their amorphous nature and highly elongated polymer chains residing within their polymeric fibers. Further, residual stresses may be generated from the dynamic "whipping" process used to produce small-diameter fibers. As typical electrospun materials undergo thermal treatments/exposure, polymer crystallization can occur, distorting fiber topography, pore size, inducing shrinkage and altering mechanical properties. For instance, in the case of poly(lactic-co-glycolic) acid ("PGLA") copolymers, such as VICRYL 90/10 PGLA, at temperatures of 37° C., shrinkage as high as 20% has been observed. This results in smaller constructs with significantly higher stiffness as well as loss of desirable chemical and mechanical properties.

What is needed in the art are improved medical devices, such as synthetic barrier materials, including but not limited to membrane applications including: tissue separation, hernia repair, peritoneum replacement, dura mater replacement, and pelvic floor reconstruction, incorporating electrospun materials that exhibit both structural and thermal stability without requiring additional processing or treatment once the fiber web or mesh is formed. The following disclosure addresses this need.

SUMMARY OF THE INVENTION

The present disclosure is directed toward generating synthetic barrier materials, including but not limited to membrane applications such as: tissue separation, hernia repair, peritoneum replacement, dura mater replacement, and pelvic floor reconstruction materials. These barrier materials offer temporal properties and functions and employ multiple fiber populations of materials including an absorbable and non-absorbable (i.e. non-degradable) material to generate a tailored mechanical behavior characteristic of the abdominal wall and/or tissue for replacement.

Nonwoven fibrous arrays are useful in the present disclosure due to their topography and size-scale, both of which mimic the extracellular matrix and offer enhanced functionality. Nonwoven materials can be produced through a variety of solution spinning applications, as known to those of skill in the art, including but not limited to electrospinning and wet-spinning.

With respect to the current disclosure, electrospinning produces fibrous materials by driving high elongational whipping of polymer solutions/melts as a means to extend the polymer reservoir into a fiber. Separate fiber populations may be used that have different morphology, topography, and mechanics, wherein one population provides initial strength upon implantation at the defect site while the second population contributes to long term elasticity and provides a permanent scaffolding barrier for tissue reconstruction and regeneration.

The present disclosure may utilize electrospun barriers, webs or fabrics and may rely on their use as a dynamic barrier material. This, coupled with at least one absorbable polymer and at least one nonabsorbable polymer, provides a barrier material system that exhibits modularity in strength, modulus (stiffness), and porosity. The current disclosure may also provide carriers for biologically active agents, while providing a dimensionally and thermally-stabilized construct, especially given the required temperature conditions including the biologically relevant 37° C., as well as 50° C. which is needed for shelf stability and sterilization processing.

Electrospun materials are of great interest for medical applications, but are limited based on their instability. What is needed are thermally stable absorbable or non-absorbable electrospun materials with little or limited macroscopic changes in physical and mechanical properties when exposed to thermal, mechanical, or other stresses. As the present disclosure explains, this may be realized through forming a barrier material that employs at least two independent fiber populations with a major fiber component comprising at least one thermally unstable species and a minor fiber component comprising at least one thermally stable species which are co-mingled and distributed throughout.

Further, the disclosed electrospun materials would not rely on downstream chemical processing or complex layered or fiber blend approaches, as known in the art, and would be superior to current technologies that employ layered constructs, cross-linked constructs, and/or creating nonwoven constructs with a core/sheath or blended fiber. Current technologies create increased production complexity due to the need for specialized equipment and cross-linking requires additional processing, such as exposure to ultraviolet light, and the introduction of additional chemical compounds that could be detrimental to product biocompatibility. The current disclosures rectifies these shortcomings.

Indeed, the current disclosure may be used to form layered, core/sheath, and/or blended fibers. One benefit of employing these constructs would be tissue ingrowth due to the presence of degradable laminates adjacent to intermixed population of bulk material. Even further, articulated surfaces may be produced wherein an aligned fiber surface is formed in contrast to a randomly aligned surface. However, randomly aligned fibers, as opposed to aligned fibers, may be used to form an adhesion surface.

In one embodiment, a thermally stable electrospun barrier may be provided. The barrier may exhibit limited macroscopic changes in physical and mechanical properties when exposed to thermal, mechanical, or other stresses. The electrospun barrier may include at least two independent fiber populations with a major fiber component comprising at least one thermally unstable species and a minor fiber component comprising at least one thermally stable species. The major and minor fiber components may be co-mingled and distributed throughout the electrospun barrier. Further, the electrospun material forms at least a portion of an implantable material.

In a further embodiment, the major fiber population may be nonabsorbable. In a yet further embodiment, the minor fiber population is absorbable. In a still yet further embodiment, the minor fiber population may be nonabsorbable. Still further, the minor fiber may have a higher crystallization temperature than the major fiber. In another embodiment, the minor fiber may have a lower crystallization temperature than the minor fiber. Yet still further, the major fiber population may have a crystallization temperature in the range of 50 to 80° C. and the minor fiber population may have a crystallization temperature in the range of 100-140° C. Even further, porosity of the barrier may be 75% or greater. Further still, the thermally stable electrospun barrier may be dimensionally stable over a range of temperatures from 30° C. to 60° C. and will not decrease in size by more than 10 percent. In a further embodiment, porosity of the thermally stable electrospun barrier may increase as the major fiber population is absorbed. Still further, the major fiber population may be derived from cyclic monomers selected from the group consisting of glycolide, lactide, caprolactone, para-dioxanone, trimethylene carbonate or mixtures thereof. Still further, the major fiber population may experience decreases in area weight or area density as it is absorbed. As the major fiber population is absorbed, the resulting fabric may have a lower area density/area weight. Ultimately, the construct may be stable and the density may be reduced by the percentage of the fast-absorbing major fabric population.

In a further embodiment, the major fiber population may be any polymer that is degradable by hydrolysis or other biodegradation mechanisms. Still further, the major fiber population may be trimethylene carbonate, lactide, glycolide, ε-caprolactone, para-dioxanone or mixtures of the above. In a still further embodiment, the major fiber population may be an absorbable PGLA copolymer with a monomer ratio of 90:10. Yet further, the minor fiber population may be a polyether-ester. In still another embodiment, the minor fiber population may be a block copolymer having one or more blocks of polydioxanone. Yet even further, polydioxanone may comprise from 10% to 80% of the copolymer. In another embodiment, the minor fiber population may be nonabsorbable and may further be poly (ethylene terephthalate). In a further embodiment, the minor fiber population may be a copolymer and the nonabsorbable fiber comprises from 10% to 80% of the copolymer.

In a still yet further embodiment, a method of forming a thermally stable electrospun is disclosed. The method may include dissolving a major fiber population in a solvent and dissolving a minor fiber population in a solvent. The dissolved major and minor fiber populations may be electrospun to form a co-spun barrier with the dissolved major and minor fiber populations dispensed through an alternating needle sequence to form an intermixed structure comprised of the major and minor fiber populations.

In a further embodiment, the major fiber population may be bioabsorbable copolymer of glycolic and lactic acid. Still further, the minor fiber population may be a bioabsorbable block copolymer having one or more blocks of polydioxanone. Even further, the barrier may be formed into a surgical mesh.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

Figure 12:
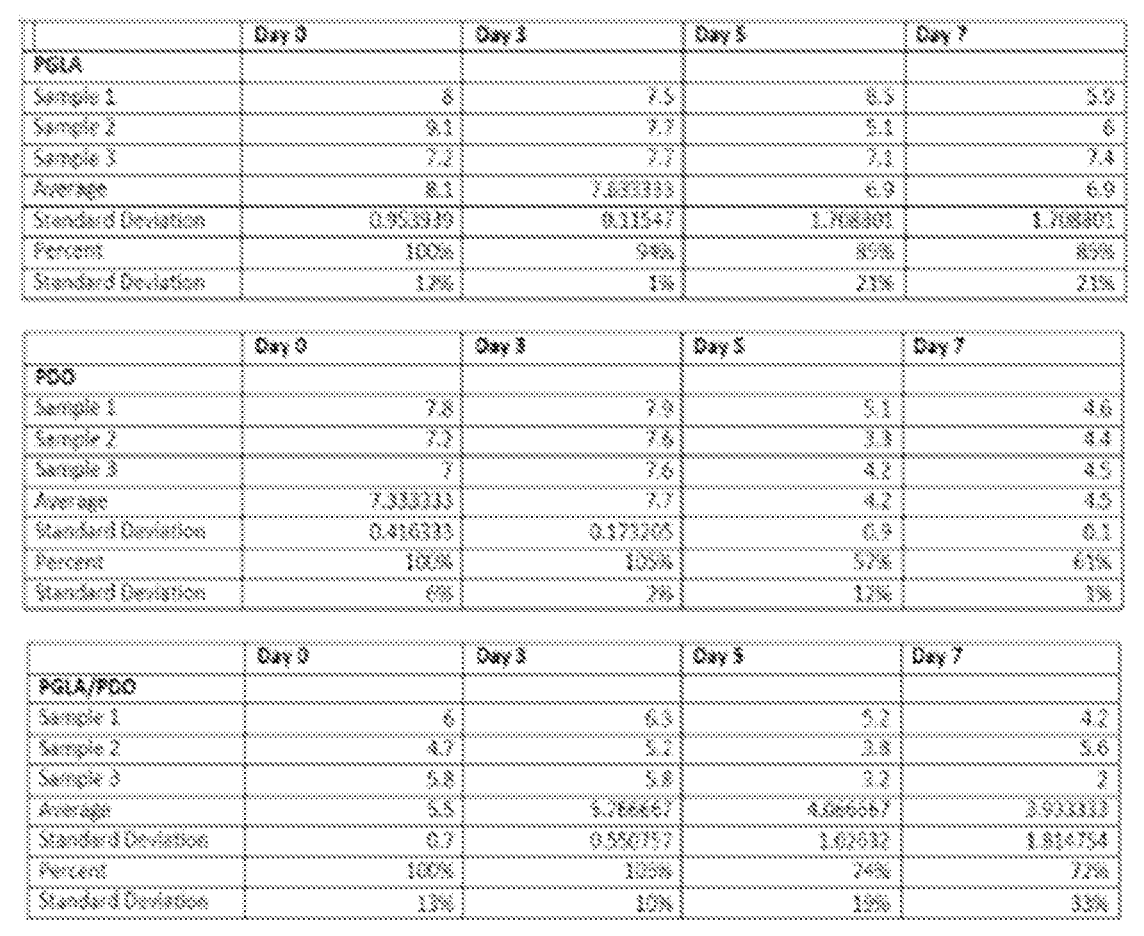

FIG. 12 shows Data Set A and its associated data.
FIG. 14 shows Data Set B and its associated data.
FIG. 17 shows Data Set D and its associated data.
FIG. 18 shows Data Set E and its associated data.

Figure 1:
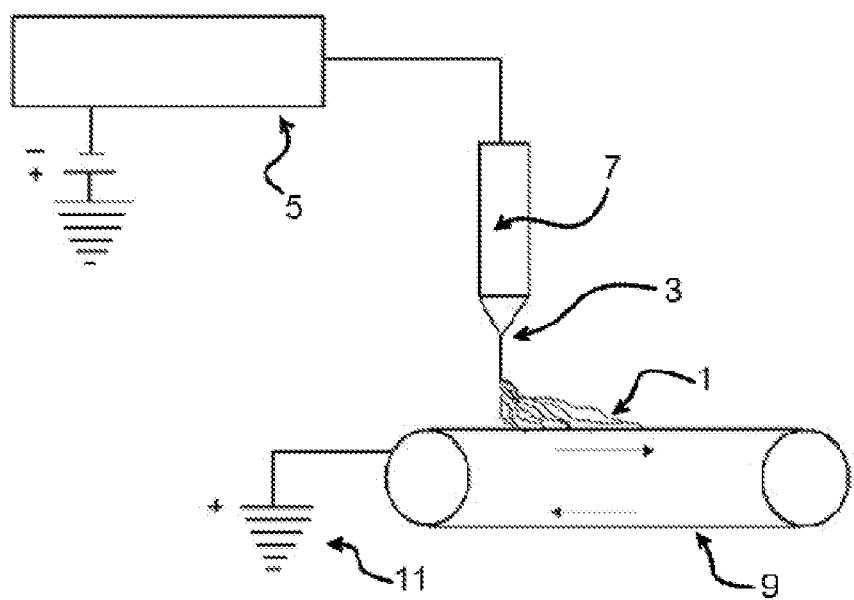
FIG. 1 is a schematic view of an electrospinning process.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

The barrier material of the present disclosure comprises at least two separate fiber populations wherein the primary or major fiber population is absorbable and provides high strength in terms of tensile strength and modulus. The primary fiber population also provides desired handling properties as it will typically comprise the bulk of the barrier, fabric or mesh.

The secondary or minor fiber population is nondegradable or nonabsorbable and provides permanent scaffolding that will remain essentially unchanged for the lifetime of the patient following absorption of the first fiber population. The secondary fiber populations may provide enhanced elasticity compared to that of the bulk device and enhanced elasticity compared to the first fiber population. Additionally, in the case wherein the second fiber population consists predominantly or entirely of polyethylene terephthalate, the second fiber population may provide a stabilizing effect by having a higher crystallization temperature comparative to the first fiber population with ranges of 50-80° C. for the first fiber population and 100-140° C. for the second fiber population. In other cases where a different non-absorbable fiber, such as polyethylene, polypropylene or a form of Nylon, is used for the second stabilizing fiber population, the crystallization temperature range may be different than that for polyethylene terephthalate. The inclusion of the secondary fiber population may provide a stabilizing effect. This effect is unexpected due to the "stabilizing" fibers providing long range stability (overall barrier dimensions) as well as short range (individual unstable fiber elements that are not necessarily bound by the other stabilizing fibers) stability.

Macroscopically, typical electrospun fibers can become distorted with a change in morphology resulting in a change in barrier pore size and handling. To overcome this limitation and minimize such changes, nondegradable fiber populations with a high Tg, ranging from 55° C. to 100° C. or greater than 100° C. can be incorporated into the barrier, when electrospun, to minimize the macroscopic effects of thermally induced crystallization to the primary absorbable fiber population. By adding a secondary fiber population, one may impart unique properties that include preferable mechanical, drape and handing properties, minimize thermally induced shrinkage, and maintain physical properties of electrospun materials in the as-formed state for in vivo application.

The present disclosure differs from other concepts to improve dimensional and thermal stability. These concepts include (1) layered fabrics, (2) cross-linking, and (3) composite fibers wherein the individual fiber comprises non-stable and stabilizing elements. Moreover, the current disclosure may provide a barrier, mesh, web, or fabric that is not comprised of an electrospun nonwoven layer deposited on top of a knit/woven structure. Instead, the current disclosure may provide an electrospun nonwoven construct that provides the totality of mechanical functionality without the need for incorporating an additional knit or woven structure.

It is important to note that the disclosed barrier, mesh, web or fabric can be produced in a 1-step process, as opposed to multi-step layering processes and complex knitting and weaving processes. It is also unusual that the electrospun construct itself is used as the mechanical component, whereas it is typically used by those of skill in the art as a coating or barrier layer in association with woven or other formed articles. Furthermore, the modulation of porosity and extensibility/modulus based on the degradation of the absorbable component is also unique in the literature. Porosity can be modulated from 75% or higher with pore sizes ranging from 1 to 300 $\mu m^2$. Extensibility of the barrier material can range from 0 to 20% for some applications, or much greater extensibility for other applications, i.e. up to 500% strain at break. For instance, extensibility may range from 20% to 100%, 50% to 100%, 100% to 200%, 150% to 200%, 200% to 300%, 250% to 300%, 300% to 400%, 350% to 400%, 400% to 500%, and from 450% to 500% including combinations of the aforementioned ranges, including but not limited to subsets of same.

In one particular embodiment, the barrier, mesh or fabric of the present disclosure comprises intermingled, small-diameter with a range of 0.1 to 20 $\mu m$, with a more preferable range of 0.5 to 10 $\mu m$, non-woven fibers comprised of at least two independent fiber populations, although more fiber populations such as three, four, five, six, etc., may be possible and are contemplated by the disclosure. Of the independent fiber populations, at least one fiber type is absorbable and at least one fiber type is non-absorbable.

In another embodiment, the barrier is dimensionally stable over a range of temperatures such as from about 30° C. to about 60° C. In a further embodiment, the barrier is dimensionally stable over the range of 35° C. to 60° C. The term "dimensionally stable" is used herein to connote that the dimensions of the barrier upon completion of formation will not change or decrease in size by more than ten percent, five percent, in some cases three percent, and in some cases not more than one percent once introduced into the patient. In another embodiment the barrier may be dimensionally stable on the microscopic level, wherein the fibers that constitute the barrier do not alter in morphology upon exposure to temperatures from 35° C. to 60° C. It is believed that by the barrier being nonwoven and containing at least one fiber population with a relatively high crystallization temperature (Tc) that this dimensionally stabilizes the barrier construct.

In a further embodiment, the barrier of the current disclosure may be produced as a nonwoven product in a 1-step process. In one preferred embodiment, the barrier may be formed as a nonwoven product via electrospinning wherein the major and minor fiber populations are employed to make a nonwoven "mat" of a desired thickness that may then be cut or otherwise formed into desired shapes and sizes. One step manufacturing can be accomplished by dispensing different fibers from separate spinnerets onto the same collector. The produced material can be of any size or shape required to treat a tissue defect. For instance, dimensions for a hernia mesh with dimensions ranging from about 1"×3" to about 5"×7" are possible. In one embodiment, the strength of the resulting materials would have an initial strength of about 16 N/cm at between about 18-32% extension for a hernia application structure.

In a further embodiment, the barrier may exhibit an initial relatively high modulus/low elasticity as compared to native tissue, i.e., the tissue in the region or area where the barrier is to be introduced for use. Over time the elasticity for the barrier material can be less than 10% with a graded increase in elasticity over a period of 4 to 128 weeks, the barrier transitions to a relatively extensible material as compared to native tissue exhibiting extensibility in the range of 20% or higher as compared to the surrounding tissue.

In a further embodiment, the structure of the barrier may be designed to initially inhibit tissue ingrowth altogether or provide for low initial tissue ingrowth. In a further embodiment, barrier materials exhibit an initial pore size in the range of 1 to 20 $\mu m$ or less for the first four weeks. Following degradation of the absorbable component the pore size increases from 20 $\mu m$ to 100 to 300 $\mu m$ dependent on ratios of the separate fiber populations. One way this may be accomplished is by controlling the porosity of the barrier by varying the ratio of the fiber populations through the thickness of the material, having a majority of the absorbable component on one side of the material with minimal nondegradable fibers and a gradual increase in nondegradable fibers throughout the thickness. As the major component degrades, the porosity of the barrier may increase up to a final porosity level that remains when the major component is completely degraded leaving only the minor component and its porosity. The differences between these porosities may range from 10 to 95%.

One embodiment of the disclosure provides that the barrier is relatively compliant and extensible after first component degrades. Degradation of the major component may be designed into the barrier based on the amount of the major component used, type of fiber used as the major component as well as combinations of these two factors. Examples of the major component can include the copolymer PGLA and the minor component can include poly (ethylene terephthalate). In one embodiment a fast degrading composition may be formed that is 90:10 PGLA or a slow degrading composition may be used that may be 88:12 Poly(lactide-co-TMC) or PLA. Ranges of polymer ratios are also within the scope of this disclosure such as 95:5, 85:15, 80:20, 75:25, 70:30, 65:35, 60:40, 55:45, and 50:50, as well as measurements within these ranges such as 89:11, 87:13, or ranges covering 95:5 to 85:15, etc. Other composition mixtures are envisioned by this disclosure and may include polymers comprised of glycolide, lactide, caprolactone, trimethylene carbonate, para dioxanone and mixtures of the above. Degradation may be selected to occur over a range of weeks, such as degrading from two to sixteen weeks. For instance, in a further embodiment, different barriers may be designed so that one barrier has a major component that is completely degraded within two weeks whereas another formulation may have a major component that degrades within sixteen weeks. The major component of the barrier may be engineered to degrade in two, three, four, five, six, seven, etc., weeks up to and including sixteen weeks. This degradation flexibility may allow for the barrier matching the modulus of the surrounding tissue with the barrier dissolving as the local tissue becomes stronger and more able to handle typical body stresses post-surgery. This avoids creating a modulus mismatch at the margins of the barrier, thereby reducing potential for re-herniation. Indeed, multiple barriers may be employed at a wound site to allow for a gradient degradation effect wherein the major component of one barrier dissolves as another barrier begins to dissolve or a first barrier may completely dissolve the major component at two weeks but an additional barrier is present wherein the major component of the barrier does not degrade until sixteen weeks.

In another aspect, the barrier may act as an adhesion prevention device. Herein, the degradation of the barrier is timed such that the major component of the barrier degrades prior to tissues or organs surrounding the wound or injury site in vivo adhering to the barrier and causing complications. Adhesion of the minor component may be mitigated by controlling fiber size, fiber roughness, fiber alignment, fiber surface characteristics, such as porosity, diameter, etc., and fiber surface coatings. Indeed, in one embodiment, early or undesired adhesion may be de-laminated based on the degradation of the absorbable component.

In a further embodiment, the barrier may be loaded with active agents, such as drugs or medicaments, as part of the spinning solution to create a delivery depot that is not a secondary coating, and which could provide release of small molecules in a time released fashion depending on the active agent and the degradation of the major component of the barrier.

[The current disclosure provides electrospun barrier materials featuring a significant reduction in shrinkage while maintaining desirable characteristics such as handling properties, mechanics, and morphology. This may be achieved by utilizing a minor polymer component providing a stabilizing effect in conjunction with a major polymer component. The stabilizing effect is unexpected due to the minor component, such as "stabilizing" fibers, providing long range stability, such as overall barrier dimensions, as well as short range stability via individual unstable fiber elements that are not necessarily bound by the other stabilizing fibers.

The current disclosure differs from prior art concepts to improve dimensional and thermal stability for electrospun materials, which include (1) layered fabrics, (2) cross-linking, and (3) composite fibers wherein the individual fiber comprises nonstable and stabilizing elements. Since many of the proposed uses of electrospun fabrics rely on the high compliance of the constructs and the use as a seal or barrier, structural integrity is of great importance. Thus, the current disclosure provides a system that may exhibit modularity in strength, modulus and porosity. This disclosure also may function as a carrier for biologically active agents like various drugs, while providing a dimensionally and thermally stabilized construct, especially under the required conditions including the biologically-relevant 37° C., as well as 50° C. which is needed for shelf stability and sterilization processing.

In a preferred embodiment, fiber distortion of an amorphous crystallizable component of a polymer is inhibited when the polymer is exposed to heat. Thermally stable absorbable fiber populations, i.e. fiber populations that do not undergo thermally induced crystallization, can be intermixed to yield a stabilizing effect without altering morphological properties of the first fiber system. Accordingly, by addition of a stabilizing fiber population one may minimize thermally induced shrinkage and maintain physical properties of electrospun materials in the as-formed state.

In a further embodiment, at least two independent fiber populations, one the major component and one the minor component, are formed from separate spinning solutions. They are used to form a barrier, mesh, web or fabric comprised of electrospun materials in a single process step without requiring further chemical or mechanical processing to impart thermal, dimensional, and mechanical stability, such as treatment by ultraviolet light or other means, introduction of crosslinking or stabilizing materials, or layering the web to improve structural integrity.

The success of the current disclosure is unexpected because the minor component changes the thermal, dimensional, and mechanical stability of the major component when the two are combined in an electrospun web. Thermally stable absorbable fiber populations, i.e. fiber populations that do not undergo thermally induced crystallization, can be intermixed to yield a stabilizing effect without altering morphological properties of the first fiber system. By addition of a stabilizing fiber population one may minimize thermally induced shrinkage and maintain physical properties of electrospun materials in the as-formed state.

These results can be explained as the stabilizing fiber population restrains the second fiber population from undergoing macroscopic changes while still allowing crystallization to occur on the molecular level within the fiber. As the intermixed fiber populated samples are exposed to thermal treatments approaching and above the Tg of the unstable fiber population, the oriented yet un-crystallized polymer chains begin to undergo molecular motion allowing for the formation of crystallites to form. This mechanism would induce the fibers to undergo morphological changes, specifically fiber contraction due to molecular reorientation.

Due to the presence of the stabilizing fiber population, the unstable fiber population is entrapped and cannot undergo restructuring that is characteristic of thermal shrinkage and dimensional changes. Though the unstabilized fiber population retains the same morphology, it is able to undergo partial or full crystallization imparted by the application of heat above its Tg. This can be evidenced by performing a differential scanning calorimetry measurement and determining the change in the enthalpy of the sample. Transition from an amorphous solid to crystalline solid is an exothermic process, and results in a peak in the DSC signal. As the temperature increases the electrospun material eventually reaches its melting temperature (Tm) resulting in an endothermic peak in the DSC curve. Materials exposed to thermal treatments that are crystallizable will show a reduction in their crystallization peak, and concomitant increase in their melting peak.

In one embodiment, the present disclosure may be a nonwoven barrier, web, mesh or fabric. Nonwoven barriers, webs, meshes, or fabrics are based on a fibrous web. The characteristics of the web determine the physical properties of the final product. These characteristics depend largely on the web geometry, which is determined by the mode of web formation. Web geometry includes the predominant fiber direction, whether oriented or random, fiber shape (straight, hooked or curled), the extent of inter-fiber engagement or entanglement, crimp and z-direction compaction/orientation. Web characteristics are also influenced by the fiber diameter, fiber welding, fiber length, fiber surface characteristics, pore size, web weight, and chemical and mechanical properties of the polymer or polymers comprising the fiber. Various ways of forming the fibrous web include spun melt, spun bond, melt blowing, solution spinning (i.e., wet spinning), centrifugal melt spinning, liquid shear spinning, and electrospinning. In one embodiment, the fibrous web is formed by electrospinning.

FIG. 1 shows a schematic diagram of electrospinning. The process makes use of electrostatic and mechanical force to spin fibers 1 from the tip of a fine orifice or spinneret 3. Spinneret 3 is maintained at positive or negative charge by a power supply 5. When the electrostatic repelling force overcomes the surface tension force of the polymer solution 7, the polymeric solution 7 spills out of spinneret 3 and forms an extremely fine continuous filament or fibers 1. These fibers 1 are collected onto a rotating or stationary collector 9 with an electrode 11 beneath of the opposite charge to that of the spinneret 3 where they accumulate and bond together to form nanofiber fabric, not shown. Multiple spinnerets providing independent, separate fiber populations may be employed. In a preferred embodiment, three spinnerets 3 may be employed. These spinnerets may each provide the same polymer, three different polymers, or one spinneret may contain a different polymer while the other two spinnerets contain the same polymer.

In one embodiment, the electrospinning apparatus includes at least one metering pump, a needle array comprised of at least two needles, at least one high voltage power supply, and a collector. The metering pump can be a syringe pump and dispenses the polymer solution at a controlled and well-defined flow rate to the needle array and can include virtually any pumping mechanism. The needle array encompasses at least two needles that dispense different polymer solutions with flow rates in the range of 0.1 to 100 ml/hr. The needle array is comprised of needles that may vary from any size (gauge) and in this example include needle sizes of 20 and 25 gauge but can include any orifice geometry or shape. The spacings between the needles may vary and, in one preferred embodiment, include spacings of at least 0.5 inches. The high voltage power supply provides sufficient voltage to overcome the surface tension of the polymer solution and may have a preferred range from +10 to +45 kV.

The current disclosure may use various ways of combining two fiber populations comprised of a polymer, copolymer, or multiple polymers into an intermingled fiber whole. For instance, possible ways of commingling fibers include electrospinning of at least two distinct and independent fiber populations from separate spinnerets, which creates intermingled fibers, where the major non-stable fiber population is stabilized by the minor fiber population. For this disclosure, major fiber, major component, or major polymer connotes a fiber, component or polymer, whether a single polymer, multiple polymers, or copolymers, that are present by in an amount ranging from greater than 30%, 35%, 40%, 45%, 50%, 55%, or 60% by weight in the resulting web or mesh. Components of the resulting mesh can vary based on the amount of polymer deposited and can be controlled by flow rate of the polymers being dispensed to form the mesh.

The distribution of the major and minor fibers may vary. The distribution may be uniform throughout the web, such as horizontally or vertically uniform or uniform throughout the thickness, length and width of the web. The distribution may also be random with the minor fiber distributed through a web of major fiber population in a random fashion. Further, the distribution may also be such that "patches" of the minor fiber are located throughout the web such that groups of the minor fibers are located in some locations but absent in others forming laminates of the minor fiber population in between the major fiber population or variations of the major and minor fiber population. In a preferred embodiment the fibers have a uniform, random dispersion throughout the resulting web in the x, y, and z directions. In a further embodiment, the ratio of major to minor component by weight may be 85/15, 80/20, 75/25, 70/30, 65/35, 60/40, 55/45, and 50/50 as well as values falling between the enumerated ratios. In a more preferred embodiment the major to minor component ration may be 67% to 33%.

The fibers of the current disclosure may comprise polymers such as polyesters, polyester-carbonates, polyethers, polyether-ester or copolymers of the above. In a further preferred embodiment, the major fiber is a bioabsorbable polymer such as a copolymer of glycolic and lactic acid such as poly (glycolic-co-lactic) acid (PGLA) and poly(lactic-co-glycolic) (PLGA), polyglycolic acid (PGA) and copolymers thereof, a polyhydroxyalkanoate (PHA) such as: polyhydroxybutyrate (PHB); poly-4-hydroxybutyrate (P4HB); polyhydroxyvalerate (PHV); polyhydroxyhexanoate (PHH); polyhydroxyoctanoate (PHO) and their copolymers, and polycaprolactone (PCL) or combinations of the above. In a further preferred embodiment, the major fiber is a bioabsorbable polyester. Additionally, any polymer that is degradable by hydrolysis or other biodegradation mechanisms and contains the following monomeric units of trimethylene carbonate, lactide, glycolide, ε-caprolactone, and para-dioxanone is applicable.

In a more preferred embodiment, the polymer is an absorbable copolymer of PGLA. In a further embodiment, the monomer ratio of glycolide to lactide in the PGLA used for the polymerization may be 95:5, 90:10, 85:15, 80:20, 75:25, 70:30, 65:35, 60:40, 55:45 or ratios between these amounts. In a preferred embodiment, the monomer ratio is 90:10. Polymerization of PGLA comprises combining the monomeric units L-lactide and glycolide at a mole ratio of 1:9 with the initiator decyl alcohol. These materials are heated to 110° C. until a homogenous mixture is formed at which point a catalyst is added at 0.05M (Tin (II) 2-ethyl hexanoate) at a final monomer to catalyst ratio of 80,000:1. The reaction is then heated to 220° C. and reacted for at least 3 hours.

The minor component may comprise thermally stable absorbable fiber populations. In one embodiment, the minor component may comprise polymers selected from polyesters, polyethers, polyether-ester or copolymers of the above. In a further embodiment, the minor component may comprise a bioabsorbable polyether-ester such as Polydioxanone (PDO). Other minor components can include co-polymers comprised of polymers where the majority of the polymer is comprised of PDO, poly(ε-caprolactone) and its copolymers, poly(L-lactic acid), amongst others. In a further embodiment, the amount of PDO may range from 10% to 80%. In a more preferred embodiment, the amount of PDO is about 33%.

In another embodiment, the minor component may be a non-absorbable fiber, including but not limited to PET, polyurethanes, polypropylene, PEEK, or different types of nylon. The nonabsorbable fiber may be present in an amount ranging from 10% to 80% with a preferred embodiment containing 33%.

Figure 2:
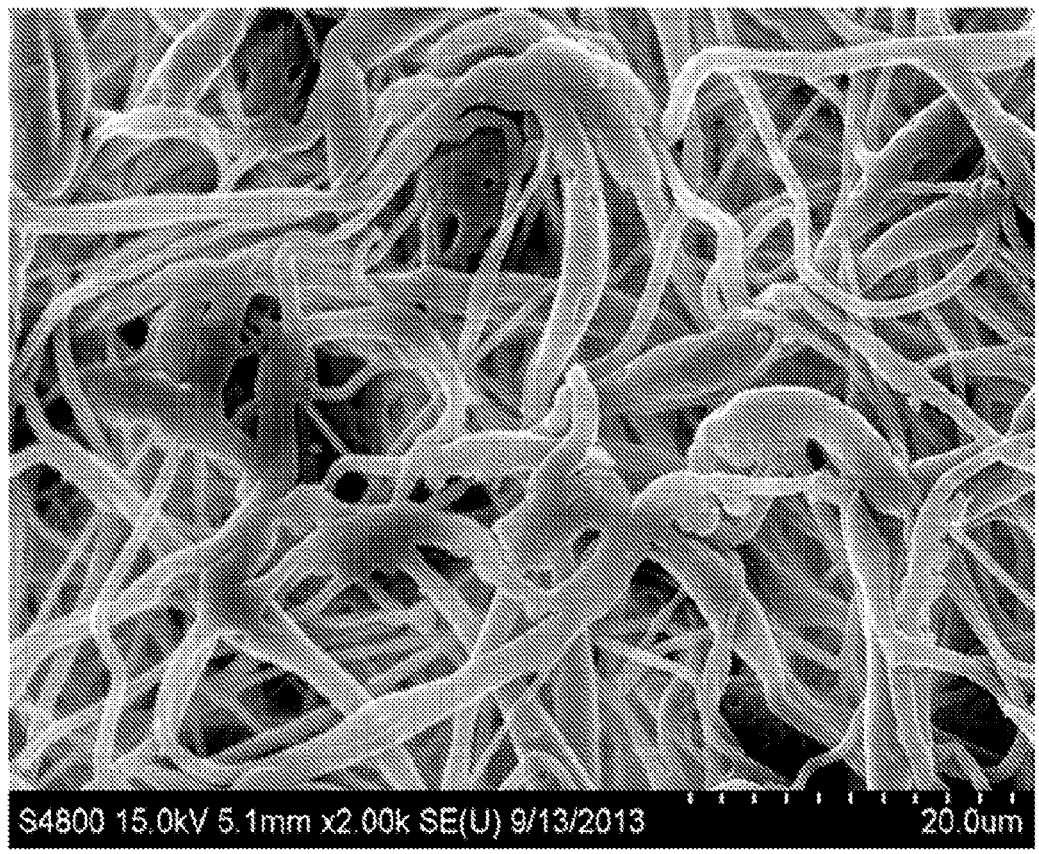
FIG. 2 shows an electron microscope view of 90/10 PGLA fibers after exposure to 45° C. for 30 minutes.

FIG. 2 shows typical 90/10 PGLA polymer fibers after exposure to 45° C. for 30 minutes. As FIG. 2 shows, the fibers exhibit structural deformities as well as clumping and gathering after thermal exposure.

Figure 3:
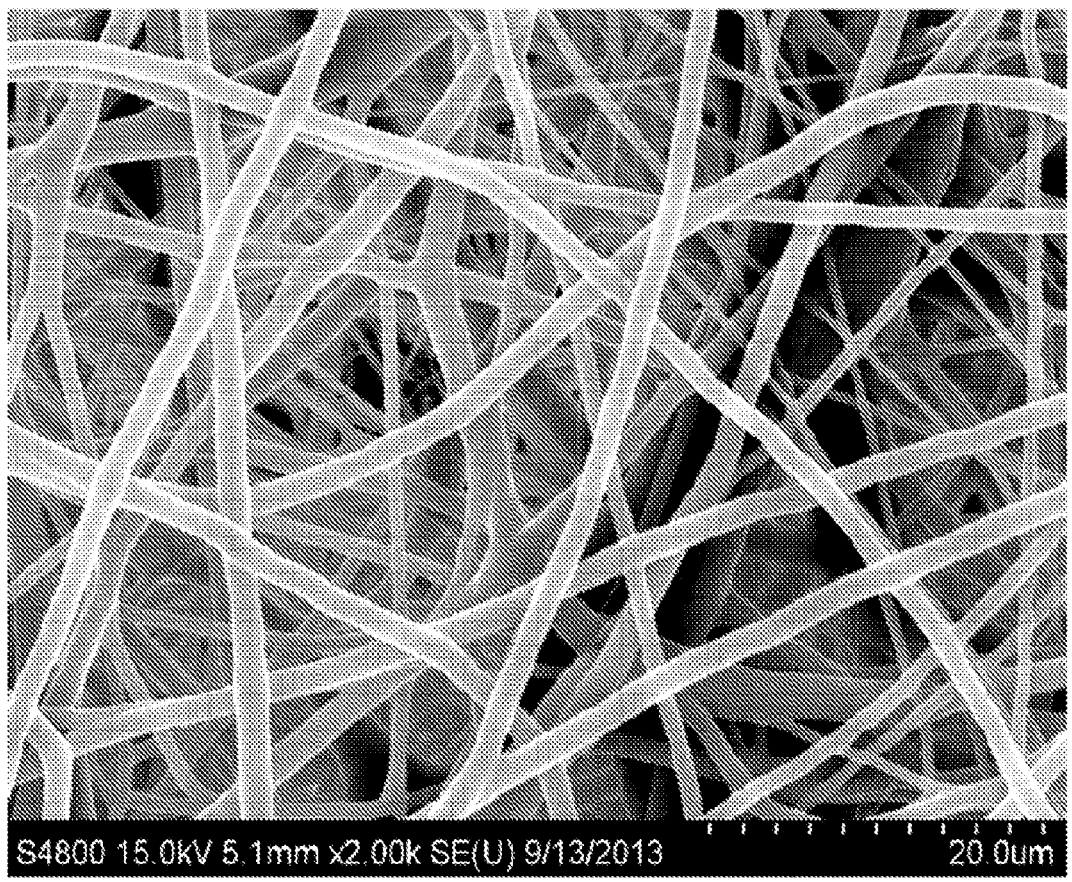
FIG. 3 shows an electron microscope view of 90/10 PGLA plus PDO cospun fibers after exposure to 45° C. for 30 minutes.

FIG. 3 shows 90/10 PGLA and PDO cospun fibers of the current disclosure after exposure to 45° C. for 30 minutes. As FIG. 3 illustrates, the fibers retain their mechanical and physical properties and do not exhibit the deformities, clumping or gathering exhibited by the 90/10 PGLA fibers. PGLA fiber meshes were formed by making an 8 wt %

PGLA (90:10) in HFIP and dissolving overnight at 50° C. Electrospun meshes were formed by depositing the solution through a 20 gauge needle array (comprised of four needles spaced 0.57 inches apart) at a flow rate of 5 ml/hr at a voltage of 22 kV. Co-spun meshes were prepared by dissolving the aforementioned PGLA and a second solution of 9 wt % PDO in HFIP and dissolving overnight at 50° C. The co-spun mesh was then produced by dispensing the different solutions through an alternating needle sequence within the needle array (two 20 gauge needles and two 25 gauge needles spaced 0.57 inches apart) to generate an intermixed population of PDO and PGLA fibers. The flow rates of the PDO and PGLA can be adjusted to generate a majority of one or the other. In this example, PDO was metered at a flow rate of 2.5 ml/hr and PGLA was metered at 5 ml/hr to generate an electrospun mesh comprised of two parts PGLA (~66%) and one part PDO (~33%).

In a further embodiment, PET may be dissolved in HFIP at 18.5 w/v %. Electrospinning may occur at a rate of 2 mL/hr from 2 needles separated by 1.14" in an electric field of 1.24 kV/com. Thermal analysis of the above method indicated a Tg for PET electrospun mesh at 55° C., peak crystallization temperature (Tc) at 146°, and peak melting temperature (Tm) at 241° C., consistent with the bulk properties of PET. Shrinkage tests of the electrospun material (45° C. for 30 minutes) resulted in a shrinkage of 0.5%, indicating a fabric that is stable at the testing temperature.

In a further embodiment, a partially absorbable co-spun may be produced. PGLA (95:5 glycolide:l-lactide) may be dissolved in HFIP at 4.8% and Polyethylene terephthalate (PET) may be dissolved in HFIP at 10.4%. Electrospinning may be performed by dispensing the different solutions through an alternating needle sequence within the needle array (all 20 gauge needles, separated by 0.57" each) to generate an intermingled population of absorbable and non-absorbable fibers. The flowrate of PGLA solution was 5 mL/hr/needle and the flowrate of PET solution was 2 mL/hr/needle. The electrospun fabric was created equal needles of PGLA and PET solutions, creating a fabric that, by weight, contained 46% PET and 54% PGLA. The fabric demonstrated the following qualities:

Fabric Thickness (mm)—0.38 mm average
Fabric Area Weight (g/cm2)—0.0068 g/cm2 average
Fabric Density (g/cm3)—0.175 g/cm3 average
PET density is 1.4 g/cm3
PGLA density is 1.4-1.6 g/cm3
Void space (%)—87.5%—supports paragraph 0029%
Shrinkage, 45° C. for 30 minutes (%)—2.7%—this is quite reduced from the typically ca. 20% shrinkage seen with PGLA fibers at these conditions
Ultimate tensile load (4-ply fabric)—17.0 N/cm—sufficient load for barrier devices, including hernia applications.
Water filter flow rate for 0.36 mm thickness-26.1 mL/min per $cm^2$—This included the method wherein a funnel containing a 100 mm column of water was positioned above a pre-wetted single layer mesh. As water passed through the samples, the flux time was measured. The flow rate calculation was made when 50 mL of water had passed through the fabric barrier and was collected in a graduated cylinder underneath. Typical knitted constructs would exhibit significantly higher flow rates and cannot act as a barrier, only as a reinforcing scaffold. The electrospun construct of this embodiment may act as both, while still allowing some level of moisture transmission which is important for tissue barrier applications.

In a further embodiment, a co-spun fully absorbable fabric may be produced. PGLA may be dissolved in HFIP at 4.8% and PPD may be dissolved in HFIP at 5.3%. Electrospinning may be conducted by dispensing the different solutions through an alternating needle sequence within the needle array (separated by 0.57" each) to generate an intermingled population of PGLA and PPD fibers. The flowrate of PGLA solution was 5 mL/hr/needle and the flowrate of PPD solution was 2.5 mL/hr/needle. The electrospun fabric was created equal needles of PGLA and PET solutions, creating a fabric that, by weight, contained 33% PPD and 67% PGLA, as well as by varying the relative number of each needle type to change the final composition.

The barrier, mesh or web disclosed herein may be used as surgical mesh, reconstruction mesh, hernia mesh, adhesion prevention barrier, drug delivery mesh, burn dressing, etc. In one instance, the fibers may be used to form all or part of a hernia mesh or patch. In a further embodiment, the barrier may be used as a hernia mesh and may be partially non-degradable, providing a permanent prophylactic protection against re-herniation at the injury site.

A hernia is a protrusion of a tissue, structure, or part of an organ through the muscle tissue or the membrane by which it is normally contained. Abdominal hernias are one common type of hernia. In an abdominal hernia, a weakness in the abdominal wall grows into a hole, or defect. Tissue may protrude from the defect. Example hernias include umbilical hernias, in which intraabdominal contents protrude through a weakness at the site of passage of the umbilical cord through the abdominal wall, and incisional hernias, which occur in an area of weakness caused by an incompletely-healed surgical wound. Those of ordinary skill in the art will appreciate that there are other types of hernias in addition to those specifically mentioned herein.

In order to treat a hernia, such as an umbilical or incisional hernia, a doctor may insert a specially designed patch into an incision near the defect. Such a patch is typically designed to be larger than the defect to ensure adequate coverage. The patch is folded or pushed through the incision. In order to allow the patch to be positioned a hernia patch may include positioning straps, which the doctor pulls on to flatten the patch once it is inside the abdominal wall. The patch is maneuvered into a flat position and moved into a suitable position, as described in more detail below. After the doctor is satisfied with the placement of the patch, the patch may be secured by suturing the positioning straps to the margins of the defect, or by suturing a part of the body of the patch to the connective tissue. Any excess material on the positioning strap is then removed and the incision is closed.

Figure 4:
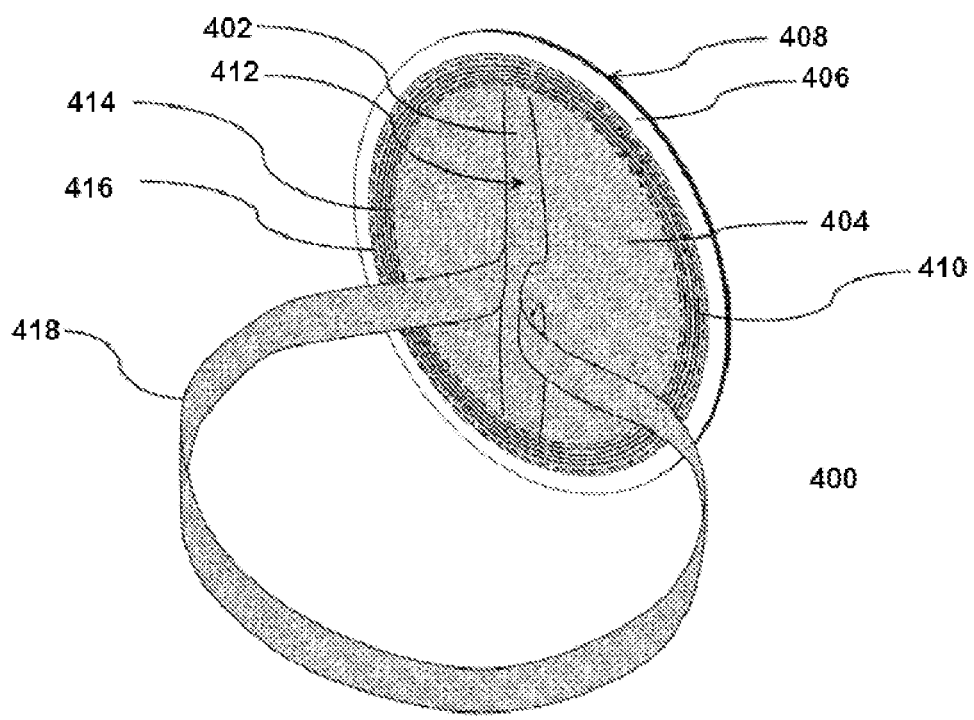
FIG. 4 depicts an example of a conventional prior art hernia patch.
Figure 5:
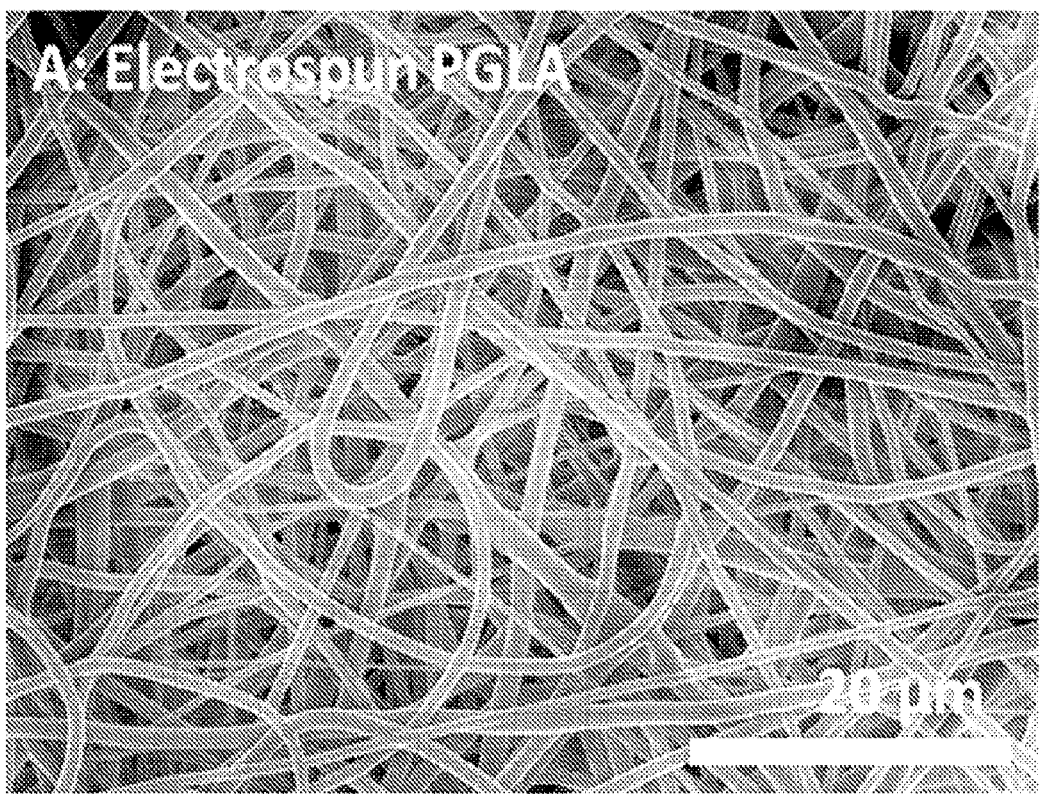
FIG. 5 shows an electron microscopy image of a PGLA fiber network without PPD.
Figure 6:
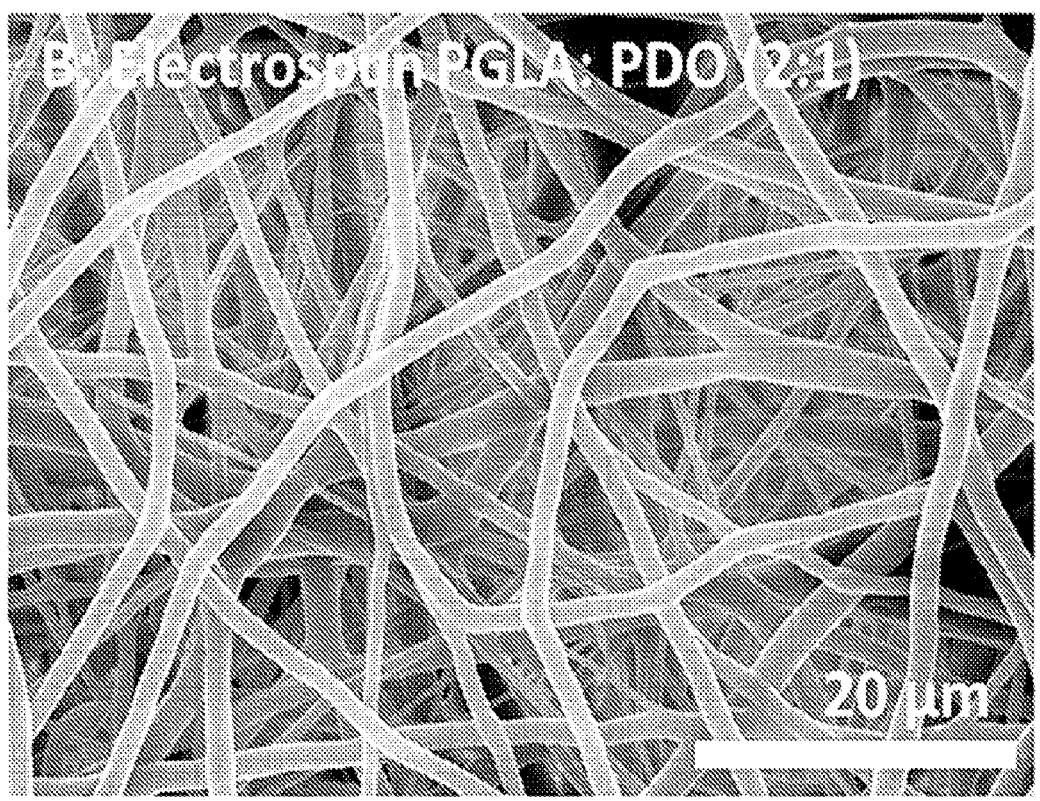
FIG. 6 shows an electron microscopy image of PGLA with PPD at a 2:1 ratio.
Figure 7:
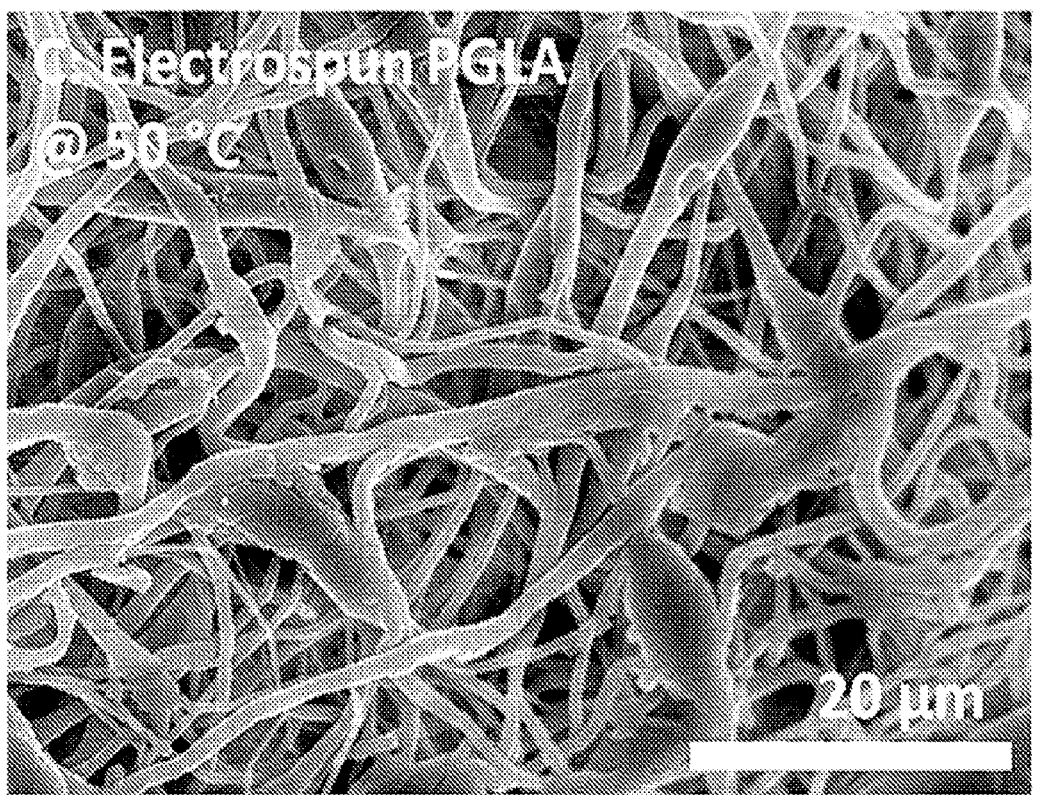
FIG. 7 shows an electron microscopy image of PGLA after being exposed to 50° C.
Figure 8:
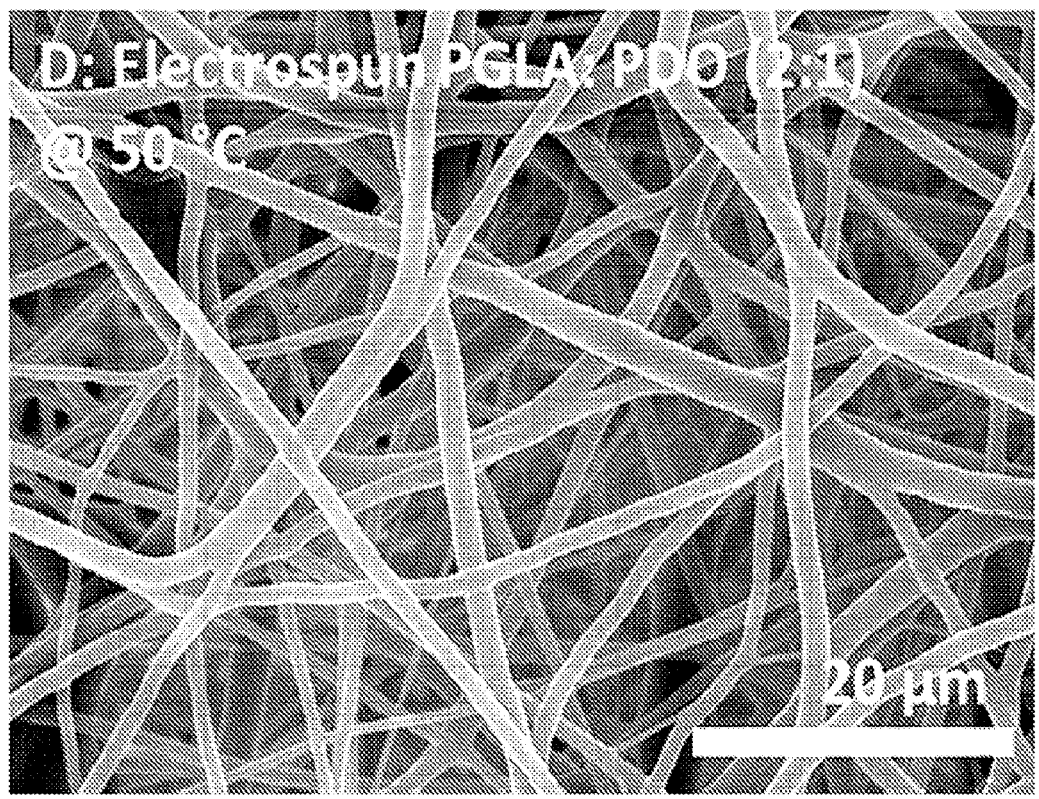
FIG. 8 shows an electron microscopy image of a PGLA/PPD composite with a 2:1 ratio after being exposed to 50° C.

One conventional type of hernia patch is made up of a round base for the patch formed from a number of layers. For example, FIG. 4 depicts an example conventional hernia patch 400. An example alternative hernia patch is made by, e.g., C.R. Bard, Inc. Warwick, R.I., such as the Ventralex™ hernia patch. As shown in FIG. 4 the base of the hernia patch 400 may be composed of three permanent polymer base layers 402, 404, and 406. One of the base layers 406 may be made of low porosity film material, and the second and third base layers 404 and 406 may be a filament knitted mesh. The smooth polymer film layer 406 is intended to act as a non-porous tissue separating layer for blocking and preventing visceral organs from coming into direct physical contact with the polymer filament mesh layers 404 and 406. The second and third base layers 402 and 404 can be formed of a single piece of material, folded over to create the two layers as described below.

In the conventional hernia patch 400, a perimeter 408 of the base is composed of a layer of polymer bonded to a layer to create polymer film layer 406. As a result, the perimeter 408 has a high degree of radial and planar stiffness, with a relatively high material density (e.g., when composed of a solid polymer).

As utilized herein, the term "stiffness" is intended to have its conventional definition of a measurement of the resistance of an elastic body to deformation when a force is applied along a given degree of freedom. Likewise, as utilized herein, the terms "flexibility" and "elasticity" relate to the ability of a material to elastically deform when a force is applied along a given degree of freedom, but not necessarily plastically deform. In other situations, some plastic deformation may occur and the measurements provided herein may include the total deformation including both elastic and plastic. A material or structure is considered to be flexible as utilized herein when the material or structure deforms with application of force, but when the force is removed, the material returns to its original shape prior to the application of force, without the requirement of heat. That is, the flexible or elastic material is not a shape memory material, which can return to its cold forged shape but only after application of heat.

This relative stiffness of the conventional hernia patch 400 means that the conventional hernia patch 400 takes its own shape and does not conform itself well to the contours of tissue, such as a patient's abdominal wall. While it does have some flexibility, such that it can be folded in half during implantation and then it will return to its original shape once the force is removed, it does not have a sufficiently high relative amount of flexibility or elasticity to respond well to the much smaller forces applied to the patch 400 as it is pressed up against a tissue wall. Further, because the densified perimeter 408 polymer structure does not possess or exhibit a sufficient macro porosity for tissue in-growth, thereby permanently limiting the material from becoming incorporated by remodeling tissue involved in healing at the implant site, these non-conforming structures often become at risk for mechanical disruption, material contraction, and/or device protrusion into other surrounding tissues following implantation. This lesser degree of tissue in-growth or cellular incorporation often leads to material encapsulation involving chronic inflammation and stimulation of dense, a-cellular connective tissue implicated in visceral organ adhesion formation between the non-porous polymer portion of the patch and the abdominal wall. Such undesirable non-healing effects have further been implicated in published reports of higher reoccurrence rates of the primary hernia repair, chronic pain, and subsequent re-intervention requirements to surgically repair the post operative complication.

In the example conventional hernia patch 400, some of its high degree of stiffness results from the existence of a monofilament polymeric stiffening ring 410 that is attached, or stitched into the periphery of the base between the two base layers 402 and 404, inside of a pocket 412 formed therebetween. The stiffening ring 410 is sewed or permanently locked into position between the two mesh layers 402 and 404. The stiffening ring 410 may be a memory material that memorizes a shape and returns to the memorized shape after being subjected to deformation. This may allow the conventional hernia patch 400 to unfold or open immediately following folded insertion through an incision. For example, in one type of hernia patch, the stiffening ring is made of either an extruded monofilament or molded polymer ring that is stitched into the periphery of the mesh base between the two polymer mesh layers 402 and 404. The stiffening ring 410 is held in tight proximity to the base materials by peripheral stitching. Alternatively, the stiffening ring 410 may be embedded in one of the base layers.

In the conventional hernia patch 400, positioning straps 418 are attached to the above-described layers of mesh to facilitate placement and fixation. The positioning straps 418 transition from the base layer 404, and the positioning straps 418 are a continuation of the same piece of mesh as the base layer 404.

In the example conventional hernia patch 400, a slit exists in the polypropylene mesh layer 404 between the two positioning straps 418. This slit provides an opening into a pocket 412 between the polypropylene mesh layers 402 and 404. When the positioning straps 418 are placed under tension, such as by pulling the straps 418 apart, the slit opens and the pocket 412 becomes accessible. A doctor may use the pocket 412 with either a finger or instrument to further deploy, flatten out, or to position the conventional hernia patch 400 once the conventional hernia patch 400 is inserted into the incision.

The conventional hernia patch 400 is stitched in two locations. An interior stitching 414 is provided in an interior part of the patch, located between the point where the straps 418 transition into the base layer 404 and the stiffening ring 410, but still close or proximal to the stiffening ring. This interior stitching penetrates through all three base layers 402, 404, and 406. An outer stitching 416 is provided between the stiffening ring and the periphery of the conventional hernia patch 400. This peripheral stitching penetrates through the two base layers 402 and 404, but not base layer 406.

Due to the above-described configuration of the stiffening ring 410, positioning straps 418, pocket 412, and stitching 414 and 416 in the conventional hernia patch 400, the above-described shortcomings regarding positioning the patch 400 and conforming the patch to the contours of the patient's abdominal wall may exist. Because the stiffening ring 410 is fixed to the base layers 404, 404 and 406 via the interior stitching 414, the straps 418 transition into the base layer 406, and a slit exists in the base layer 406 between the straps 418, when tension is applied by the straps as they are pulled up and out through the hernia defect for suture fixation outside of the abdominal cavity, but within the incision of the abdominal wall, the center of the conventional hernia patch 400 pulls up into the hernia defect while the perimeter of the conventional hernia patch 400 ends to separate away from the tissue wall adjacent to the hernia defect with which it is meant to be in direct contact. This creates a large open space between the base layers 404 and 402 that can delay tissue in-growth and healing. When this required tension is applied to these straps for device positioning and fixation, it causes significant separation of the material layers and formation of the pocket 412. The indwelling intra-abdominal cavity portion of the base layer material of the conventional hernia patch 400 tends to yield to the tension applied by the positioning and fixation straps by stretching upward, lifting and bending away from the abdominal wall. This creates a non-uniform and/or irregular shaped surface profile that is often a substantially conical shape in appearance, leaving an undesirable gap or open space between the perimeter body of the conventional hernia patch 400 and the abdominal wall. This space becomes difficult for tissue to heal across, thereby requiring greater lengths of time for connective tissue to fill in between the perimeter rim of the patch. Such spaces can further lead to complications of visceral organ entrapment involved with adhesion formation.

The present disclosure provides, in one embodiment, a more simple barrier design, such as in one preferred embodiment where an electrospun nonwoven hernia barrier is formed in a single step processing method that is vastly superior to the process used to form the hernia patch shown in FIG. 4. When further taking into consideration the embodiments employing degradable and nondegradable fibers working in unison, the present embodiment satisfies a long felt need in the medical industry to aid in hernia barrier placement, reduce stress on the patient, as well as to promote healing while reducing the worries of infection, unwanted tissue growth, and failing to allow sufficient time for the patient's tissues to recover from the wound before the barrier degrades and/or loses strength. The benefit of the combination of intermixed fiber populations allows for the selective removal of the absorbable component which, in turn, increases the porosity and extensibility of the implant, approximating the biological properties of the native tissue while allowing for cellular ingrowth and deposition of extracellular matrix to strengthen the tissue defect and integrate the implant into the surrounding tissue.

In one comparative example, PGLA and PPD solutions were deposited from an array of separate 20 gauge needles at varying flow rates between 1 and 12 mL/hour. Composite materials were generated with the following PGLA:PPD ratios 2:0, 2:1, 1:1, 1:2, and 0:2. These ratios can be generated by multiple methods, or a combination of methods, which include varying: (1) the relative number of needles, (2) individual needle flow rates, and (3) solution concentrations. In this particular example, solution concentrations remained constant and the number of needles was varied to generate the various compositions. The resulting fabric contained well-defined and relatively uniform small-diameter fibers deposited in a randomly oriented fibrous mat. Differences between PGLA and PPD fibers were not obvious based on SEM and light microscopy, but the presence of fibers without significant size and deformation indicate that fibers formed from the individual solutions and contain only one material, as opposed to very large fibers or inconsistent/film-like morphology which could be associated with solution blending. These electrospun samples were assessed for morphology, tensile mechanics, free shrinkage, and crystallization. Tables A-D illustrate the characteristics of the resulting fibers and the data sets below each table identify the samples used to provide the data illustrated in the respective Tables. The data marked by the * symbol shows significant deviation in properties from the PGLA control group.

As the above data illustrate, electrospun materials were fabricated from PGLA, PPD and composites containing both. All samples exhibited fibrous morphology with submicron fiber diameters (<1 μm). FIGS. 5-8 illustrate the fibrous morphology as well as the impact of exposure to 50° C. conditions to same. As the data shows, inclusion of increasing PPD amounts results in thermally stable fabric, such as that shown in FIG. 8. Comparatively, neat PGLA displayed contraction in pore size and disordered fiber morphology resultant of crystallization within the fiber, see FIG. 7. Incorporation of PPD into PGLA at all loading levels, led to maintenance of both fiber morphology and pore size, see FIG. 8. Free shrinkage of electrospun PGLA without PPD, see FIG. 7, possessed an average contraction of 22±8% while inclusion of PPD at 33% loading content significantly lowered this to 6±3%, see FIG. 8. At PPD levels of >50%, free shrinkage decreased to less than 2%.

Figure 9:
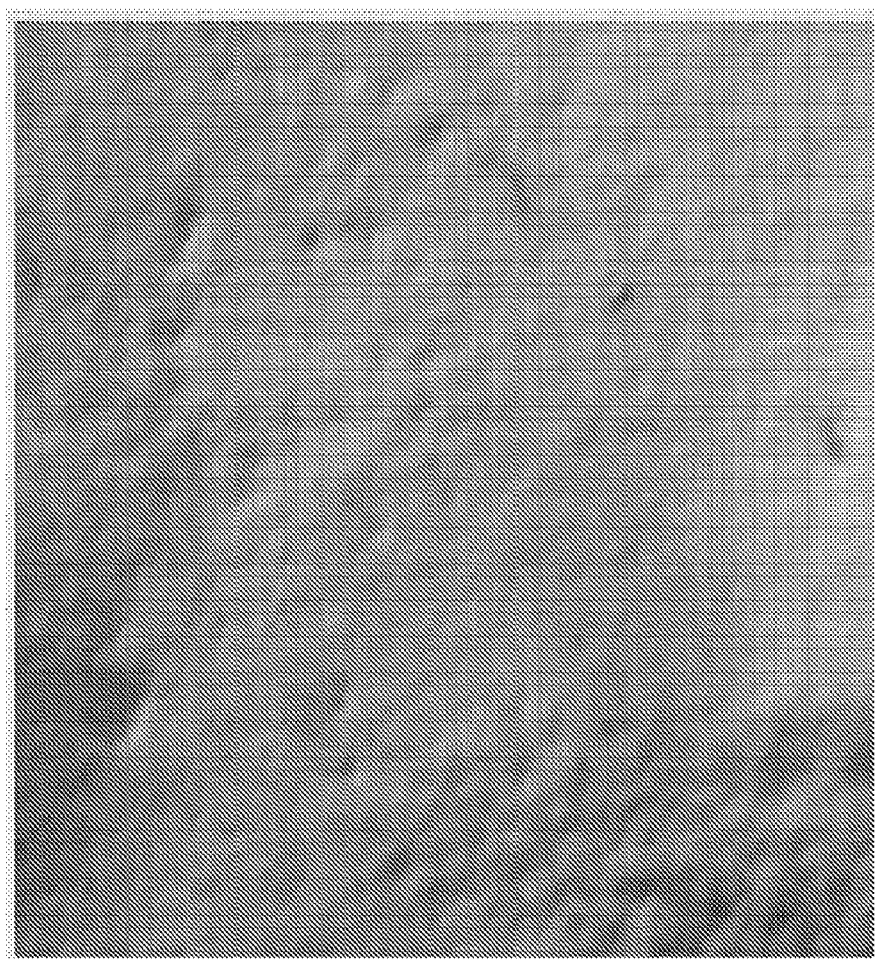
FIG. 9 demonstrates an electrospun construct of the present disclosure made at room temperature.
Figure 10:
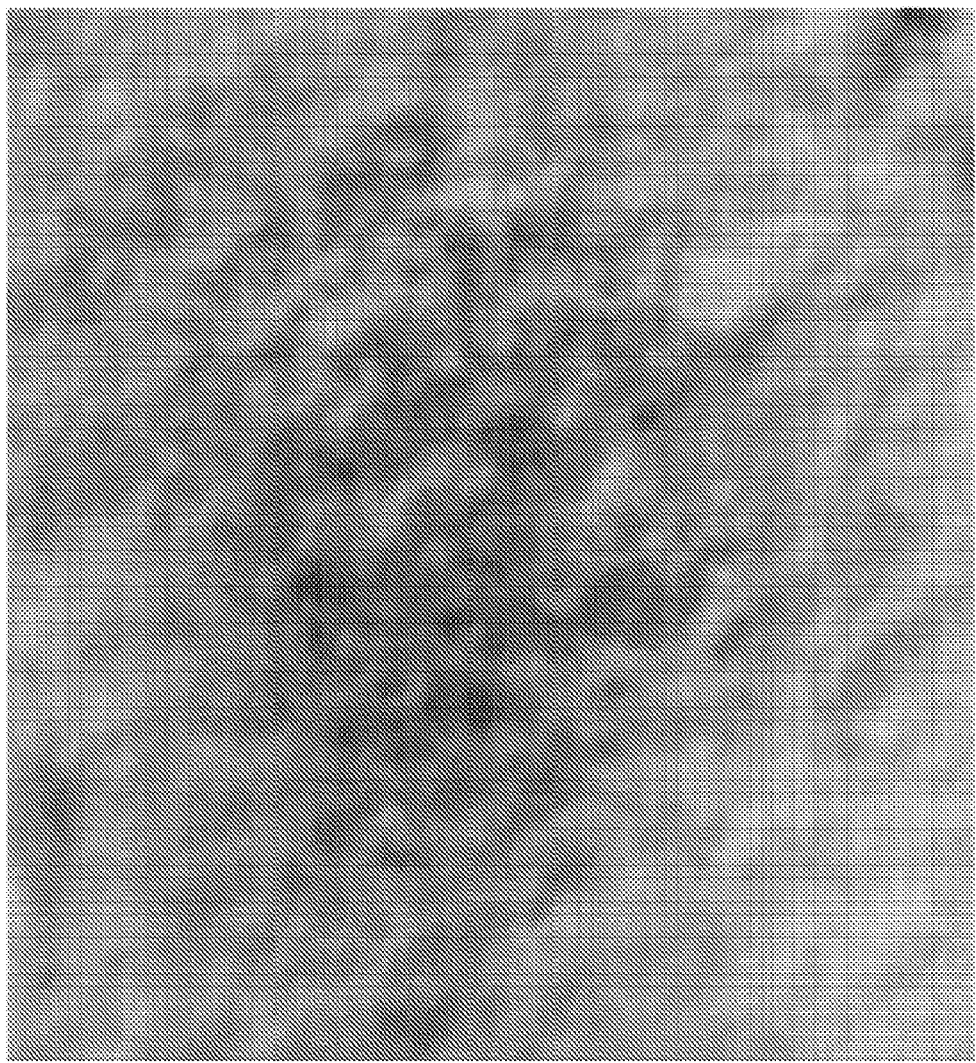
[FIG. 10 demonstrates an electrospun construct of the present disclosure formed at −80° C.
Figure 11:
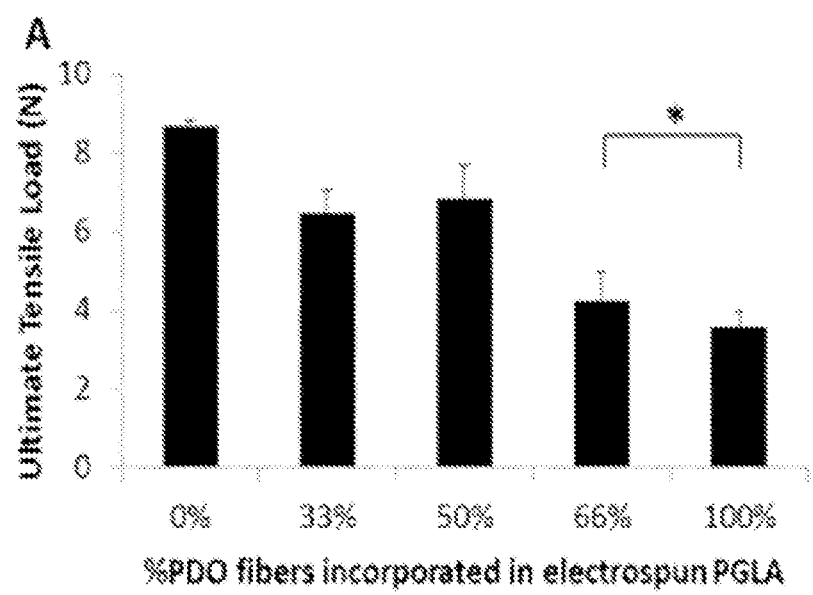
FIG. 11 shows Table A and its associated data.
Figure 13:
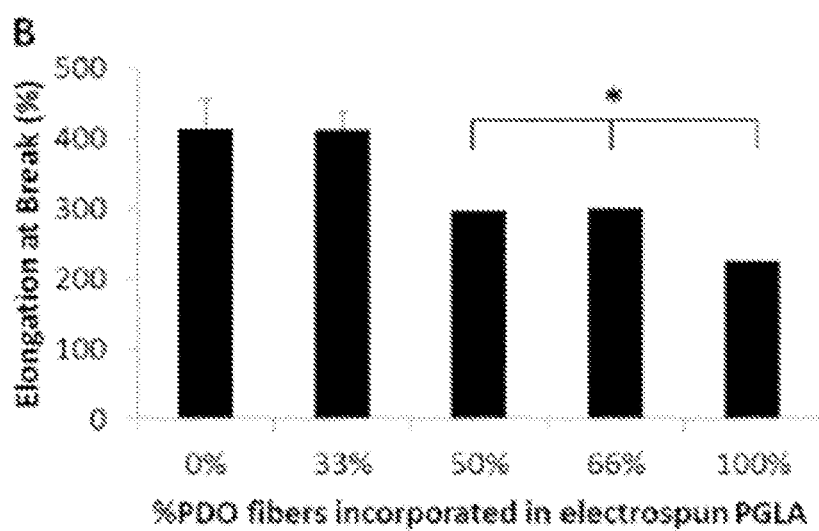
FIG. 13 shows Table B and its associated data.
Figure 15:
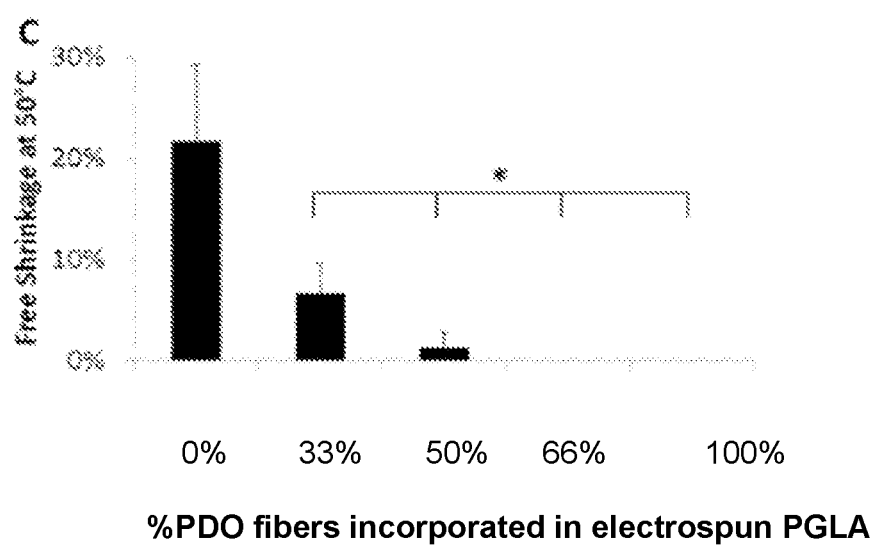
FIG. 15 shows Table C and its associated data.
Figure 16:
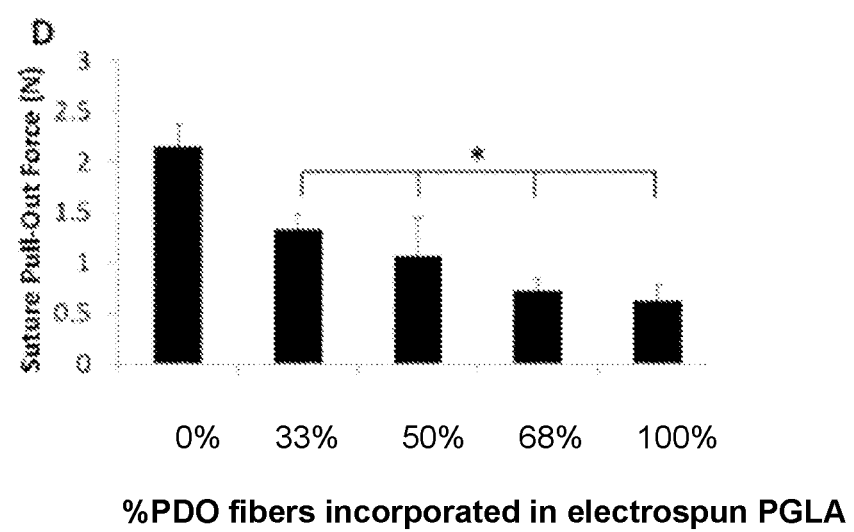
FIG. 16 shows Table D and its associated data.
Figure 19:
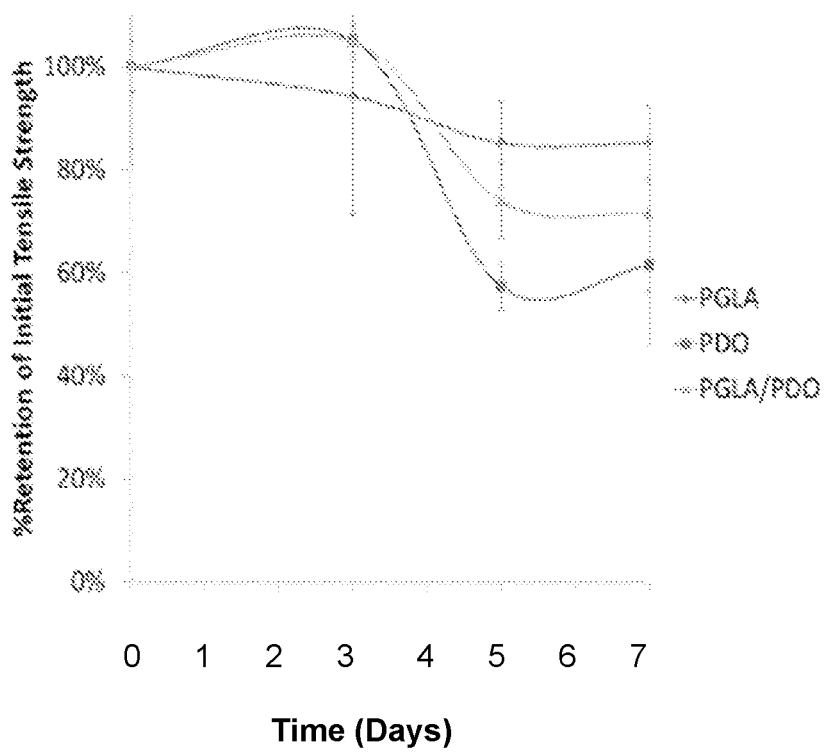
FIG. 19 is Graph A and its associated data.
Figure 20:
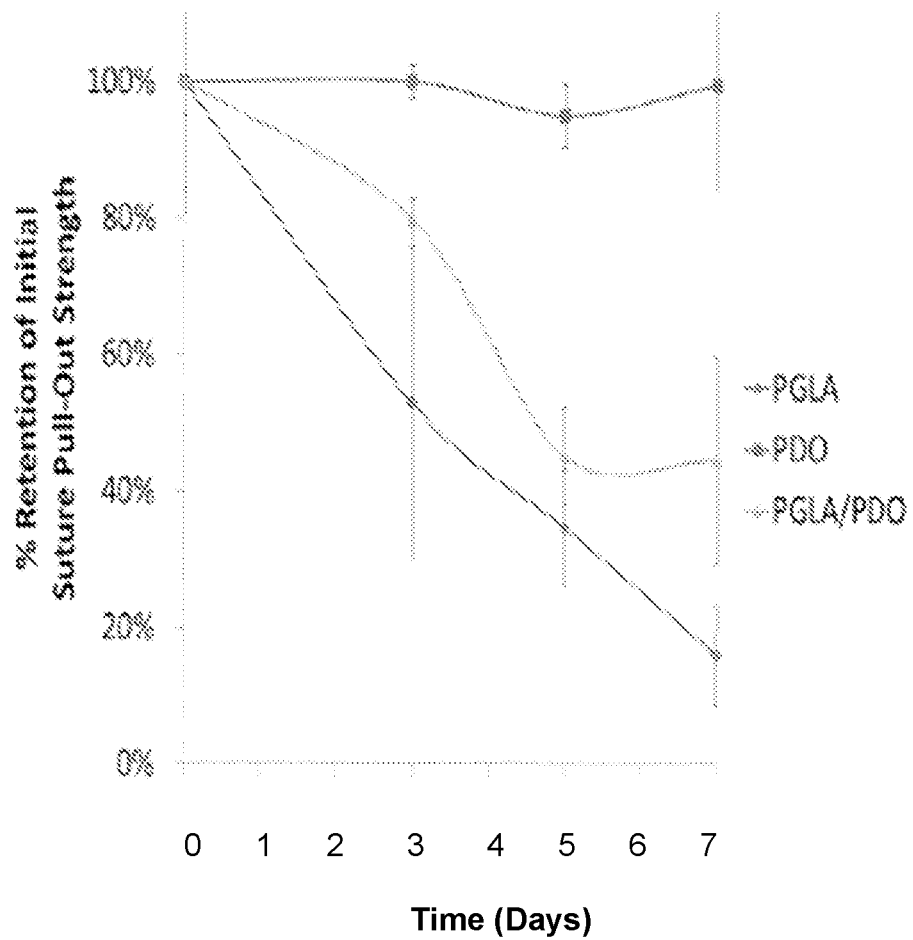
FIG. 20 is Graph B and its associated data.
Figure 21:
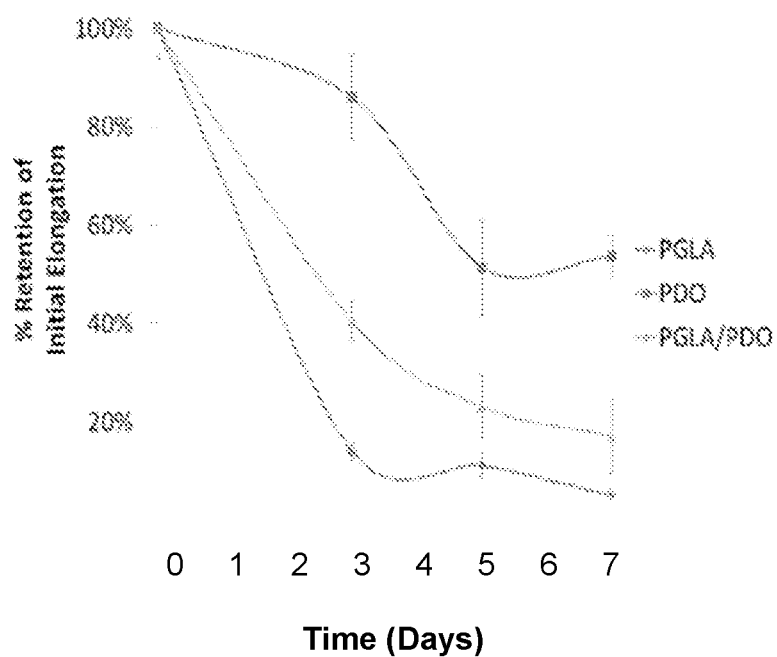
FIG. 21 is Graph C and its associated data.

FIGS. 9 and 10 demonstrate the bulk differences in electrospun constructs of the present disclosure made at room temperature, FIG. 9, and at −80° C., FIG. 10. It is apparent that the construct made at room temperature is relatively smooth, whereas the construct made at −80° C. has a fluffy, porous texture. The FIG. 9 construct may be used as a barrier membrane and may exhibit limited cell ingress, increased strength, lower pore size, and lower porosity. Meanwhile, the FIG. 10 construct may exhibit increased pore size, increased porosity, may allow for better cellular ingress and cellular attachment, as well as may allow for better extracellular matrix production/accumulation and may exhibit lower overall strength.

In a further embodiment, PGLA was dissolved in HFIP at 4.8% and PPD was dissolved in HFIP at 5.3%. Electrospinning was conducted by dispensing the different solutions through an alternating needle sequence within the needle array (separated by 0.57" each) to generate an intermingled population of PGLA and PPD fibers. The flowrate of PGLA solution was 5 mL/hr/needle and the flowrate of PPD solution was 2.5 mL/hr/needle. The electrospun fabric was created with equal needles of PGLA and PET solutions, creating a fabric that, by weight, contained 33% PPD and 67% PGLA, as well as by varying the relative number of each needle type to change the final composition.

Mechanical analysis indicated that incorporation of PPD decreased the ultimate tensile load and elongation at high content levels, such as >50% while suture pull-out was lowered at all loading levels with PPD>33%. In a preferred embodiment, PPD of 33% exhibits the optimal mechanical properties while minimizing thermal shrinkage. DSC analysis indicated that thermally treated samples had a reduction in crystallization peak, not shown.

Graphs A, B and C, below, show the results of mechanical testing over seven days under in vitro conditions. As Graph A shows, PGLA maintained tensile strength over seven days in vitro, but lost suture pull-out strength and elongation at break, see Graphs B and C. Reduction in elongation may be attributed to the thermally sensitive and amorphous nature of the material. PPD, meanwhile, exhibited loss of tensile strength, see Graph A, but maintained suture pull-out strength, see Graph B, and a slight reduction in elongation at break, see Graph C. The composite PGLA:PPD system exhibited intermediate properties between PGLA and PPD expressing hybrid properties between both systems.

Graph A

Graph A shows percent retention of initial tensile strength over seven days in vitro. PGLA maintained tensile strength while PPD and the composite system demonstrated a reduction in tensile strength.

Graph B

Graph B shows initial suture pull-out strength over seven days in vitro. PPD maintained suture pull-out strength throughout the seven day period while PGLA and the composite system demonstrated reduction in pull out strength.

Graph C

Graph C shows percent retention of initial elongation over seven days in vitro. PGLA demonstrated significant reduction in elongation which may be due to molecular reorganization in electrospun fibers, resulting in brittle material.

In one embodiment, the electrospun fabrics may have a three-dimensional structure. In a further embodiment, the fiber populations may be dispersed throughout the three dimensional structure such that the relative ratios of the fibers to one another remains substantially constant throughout the structure of the fabric. In other embodiments, the structure of the fabric may be modified such that the ratios of the fabrics to one another vary throughout the structure, such as one fiber being predominately present on the exteriors of the three dimensional structure but less present, or lacking altogether, in the interior of the structure.

As the data shows, PPD may serve to stabilize the dimensions of electrospun fabrics upon exposure to heat while maintaining mechanical properties. In those examples where PPD was not present, the electrospun fabric undergoes changes in physical properties in the presence of heat, such as significantly marked shrinking. For example Table C shows the percent free shrinkage is greater than 20% when the electrospun PGLA fabric contains no PPD. The ultimate tensile load, elongation at break, and suture pull-out force as shown by Tables A, B, and D also demonstrate the effects of PPD incorporated into electrospun PGLA. However, use of varying fiber populations may produce robust, thermally stable electrospun materials and may influence long term mechanical performance providing temporal properties with respect to mechanics, resorption, and biological response. In an further embodiment, when reviewing Table C the percent free shrinkage at 50° C. is reduced by at least 50% by the incorporation of a stabilizing fiber population. PGLA alone has free shrinkage of at least 20-30%. Further, incorporation of 33% into electrospun PGLA results in free shrinkage of less than 10% at 50° C.

In some embodiments, the barrier, web, mesh or fabric of the present disclosure may further comprise one or more bioactive or therapeutic agents, as well as methods of delivering therapeutic agents. The method comprises the step of applying a mesh or web at a treatment site wherein the polymers of the mesh or web comprise at least one base polymer and one or more bioactive and/or therapeutic agents. Biocompatible polymeric compositions containing a therapeutic agent can be prepared by the cold-worked or hot-worked method, depending on the heat-resistance of the therapeutic agent. For therapeutic agents that are likely to be inactivated by heat, the cold-worked method is preferred. Briefly, the polymer components of the mesh or web, either the major component, the minor component or both, may be completely melted in the absence of the therapeutic agent. The melted composition is cooled to room temperature or below to delay crystallization of the polymer in the composition. In certain embodiments, the cooling is conducted at a rate of about 10° C. per minute. The therapeutic agent is then added to the melted composition at room temperature or below and mixed thoroughly with the composition to create a homogeneous blend. Solution-based mixing procedures may also be employed depending on the nature of the materials.

In an alternative embodiment, the barrier, mesh or web of the current disclosure may have the bioactive and/or therapeutic agents applied to one or more specific sections of the mesh or web, as opposed to the entire construct. Within certain embodiments, the mesh or web can be either dip-coated or spray-coated with one or more bioactive agents, or with a composition which releases one or more bioactive agents over a desired time frame. In yet other embodiments, the fibers themselves may be constructed to release the bioactive agent(s) (see e.g., U.S. Pat. No. 8,128,954 which is incorporated by reference in its entirety).

The therapeutic agents may include fibrosis-inducing agents, antifungal agents, antibacterial agents, anti-inflammatory agents, anti-adhesion agents, osteogenesis and calcification promoting agents, antibacterial agents and antibiotics, immunosuppressive agents, immunostimulatory agents, antiseptics, anesthetics, antioxidants, cell/tissue growth promoting factors, lipopolysaccharide complexing agents, peroxides, anti-scarring agents, anti-neoplastic, anti-cancer agents and agents that support ECM integration.

Examples of fibrosis-inducing agents include, but are not limited to talcum powder, metallic beryllium and oxides thereof, copper, silk, silica, crystalline silicates, talc, quartz dust, and ethanol; a component of extracellular matrix selected from fibronectin, collagen, fibrin, or fibrinogen; a polymer selected from the group consisting of polylysine, poly(ethylene-co-vinylacetate), chitosan, N-carboxybutyl-chitosan, RGD proteins, and any peptide sequence greater than one amino acid in length; vinyl chloride or a polymer of vinyl chloride; an adhesive selected from the group consisting of cyanoacrylates and crosslinked poly(ethylene glycol)-methylated collagen; an inflammatory cytokine (e.g., TGF.beta., PDGF, VEGF, bFGF, TNF.alpha., NGF, GM-CSF, IGF-a, IL-1, IL-1-.beta., IL-8, IL-6, and growth hormone); connective tissue growth factor (CTGF); a bone morphogenic protein (BMP) (e.g., BMP-2, BMP-3, BMP-4, BMP-5, BMP-6, or BMP-7); leptin, and bleomycin or an analogue or derivative thereof. Optionally, the device may additionally comprise a proliferative agent that stimulates cellular proliferation. Examples of proliferative agents include: dexamethasone, isotretinoin (13-cis retinoic acid), 17-e-estradiol, estradiol, 1-a-25 dihydroxyvitamin D3, diethylstibesterol, cyclosporine A, L-NAME, all-trans retinoic acid (ATRA), and analogues and derivatives thereof, (see US Pat. Pub. No. 2006/0240063, which is incorporated by reference in its entirety).

Examples of antifungal agents include, but are not limited to polyene antifungals, azole antifungal drugs, and Echinocandins.

Examples of antibacterial agents and antibiotics include, but are not limited to erythromycin, penicillins, cephalosporins, doxycycline, gentamicin, vancomycin, tobramycin, clindamycin, and mitomycin.

Examples of anti-inflammatory agents include, but are not limited to non-steroidal anti-inflammatory drugs such as ketorolac, naproxen, diclofenac sodium and flurbiprofen.

Examples of anti-adhesion agents include, but are not limited to talcum powder, metallic beryllium and oxides thereof, copper, silk, silica, crystalline silicates, talc, quartz dust, and ethanol.

Examples of osteogenesis or calcification promoting agents include, but are not limited to bone fillers such as hydroxyapatite, tricalcium phosphate, calcium chloride, calcium carbonate, calcium sulfate, bioactive glasses, bone morphogenic proteins (BMPs), such as BMP-2, BMP-3, BMP-4, BMP-5, BMP-6, and BMP-7.

Examples of immunosuppressive agents include, but are not limited to glucocorticoids, alkylating agents, antimetabolites, and drugs acting on immunophilins such as ciclosporin and tacrolimus.

Examples of immunostimulatory agents include, but are not limited to interleukins, interferon, cytokines, toll-like receptor (TLR) agonists, cytokine receptor agonist, CD40 agonist, Fc receptor agonist, CpG-containing immunostimulatory nucleic acid, complement receptor agonist, or an adjuvant.

Examples of antiseptics include, but are not limited to chlorhexidine and tibezonium iodide.

Examples of antioxidants include, but are not limited to antioxidant vitamins, carotenoids, and flavonoids.

Examples of anesthetic include, but are not limited to lidocaine, mepivacaine, pyrrocaine, bupivacaine, prilocalne, and etidocaine.

Examples of cell growth promoting factors include but are not limited to, epidermal growth factors, human platelet derived tgf-b, endothelial cell growth factors, thymocyte-activating factors, platelet derived growth factors, fibroblast growth factor, fibronectin or laminin.

Examples of lipopolysaccharide complexing agents include, but are not limited to polymyxin.

Examples of peroxides, include, but are not limited to benzoyl peroxide and hydrogen peroxide.

Examples of antineoplastic/anti-cancer agents include, but are not limited to paclitaxel, carboplatin, miconazole, leflunamide, and ciprofloxacin.

Examples of anti-scarring agents include, but are not limited to cell-cycle inhibitors such as a taxane, immunomodulatory agents such as serolimus or biolimus (see, e.g., paras. 64 to 363, as well as all of us U.S. Pat. Pub. No. 2005/0149158, which is incorporated herein by reference in its entirety).

Examples of agents that support ECM integration include, but are not limited to gentamicin.

It is recognized that in certain forms of therapy, combinations of agents/drugs in the same polymeric composition can be useful in order to obtain an optimal effect. Thus, for example, an antibacterial and an anti-inflammatory agent may be combined in a single copolymer to provide combined effectiveness.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A thermally stable electrospun barrier comprising: two independent fiber populations;
   a major fiber population comprising at least one thermally unstable fiber species, wherein the thermally unstable fiber species comprises polymers or copolymers that are degradable by hydrolysis or other biodegradation mechanisms; are derived from cyclic monomers selected from the group consisting of glycolide, lactide, caprolactone, para-dioxanone, trimethylene carbonate, and mixtures thereof;
   a minor fiber population comprising at least one thermally stable fiber species, wherein the thermally stable fiber species comprises polymers or copolymers selected from polyesters, polyethers, polyester-carbonates, polyether-ester or copolymers thereof, a block copolymer having one or more blocks of polydioxanone (PDO), co-polymers comprised of polymers where the majority of the polymer is comprised of PDO, poly(E-caprolactone) and its copolymers, poly(L-lactic acid), poly(ethylene terephthalate), polyethylene, polypropylene, a nylon, polyurethanes, or PEEK;
   wherein the major and minor fiber populations are co-mingled and distributed throughout the electrospun barrier;
   wherein each fiber population does not comprise a composite fiber wherein neither a polymer or copolymer forming a thermally stable fiber species is present in a thermally unstable fiber species, nor is a polymer or copolymer forming a thermally unstable fiber species present in a thermally stable fiber species;
   wherein the thermally stable species comprises 13 wt % to up to 49 wt % percent of the thermally stable electrospun material;
   wherein each fiber population is dispensed from a spinneret separate from the spinneret of another fiber population so that none of the thermally stable fiber species are present in the population of the thermally stable fiber population and none of the thermally unstable fiber species are present in the thermally unstable fiber population; and
   wherein the electrospun barrier is dimensionally stable up to 5.0° C. and under these temperature conditions, will not decrease in size by more than 10 percent.

2. The thermally stable electrospun barrier of claim 1, wherein the major fiber population is absorbable.

3. The thermally stable electrospun barrier of claim 1, wherein the minor fiber population has a higher crystallization temperature than the major fiber population.

4. The thermally stable electrospun barrier of claim 3, wherein the major fiber population has a crystallization temperature in the range of 50 to 80° C. and the minor fiber population has a crystallization temperature in the range of 100-140° C.

5. The thermally stable electrospun barrier of claim 1, wherein porosity is 75% or greater.

6. The thermally stable electrospun barrier of claim 1, wherein porosity of the thermally stable electrospun barrier increases as the major fiber population is absorbed.

7. The thermally stable electrospun barrier of claim 1, wherein the major fiber population is an absorbable copolymer of glycolide and lactide.

8. The thermally stable electrospun barrier of claim 7, wherein the major fiber population is an absorbable PGLA copolymer with a monomer ratio of glycolide to lactide of about 90:10.

9. The thermally stable electrospun barrier of claim 1, wherein the minor fiber population is nonabsorbable.

10. The thermally stable electrospun barrier of claim 9, wherein the nonabsorbable fiber is poly(ethylene terephthalate).

* * * * *